United States Patent
Marks et al.

(10) Patent No.: US 9,943,463 B2
(45) Date of Patent: Apr. 17, 2018

(54) MEDICAL DEVICES INCLUDING VIAL ADAPTER WITH INLINE DRY DRUG MODULE

(71) Applicant: MEDIMOP Medical Projects Ltd., Ra'anana (IL)

(72) Inventors: Hugh Zachary Marks, Summit, NJ (US); Nimrod Lev, Savion (IL); Amir Lev, Kfar Saba (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 343 days.

(21) Appl. No.: 14/888,590

(22) PCT Filed: May 5, 2014

(86) PCT No.: PCT/IL2014/050405
§ 371 (c)(1),
(2) Date: Nov. 2, 2015

(87) PCT Pub. No.: WO2014/181328
PCT Pub. Date: Nov. 13, 2014

(65) Prior Publication Data
US 2016/0081878 A1    Mar. 24, 2016

Related U.S. Application Data

(60) Provisional application No. 61/821,760, filed on May 10, 2013.

(51) Int. Cl.
*A61B 19/00* (2006.01)
*A61J 1/20* (2006.01)
*A61M 5/28* (2006.01)

(52) U.S. Cl.
CPC .............. *A61J 1/2096* (2013.01); *A61J 1/201* (2015.05); *A61J 1/2075* (2015.05); *A61J 1/2082* (2015.05);
(Continued)

(58) Field of Classification Search
CPC ........ A61J 1/2096; A61J 1/201; A61J 1/2075; A61J 1/2082; A61M 5/284; A61M 2209/045
(Continued)

(56) References Cited

U.S. PATENT DOCUMENTS

| | | | |
|---|---|---|---|
| 62,333 | A | 2/1867 | Holl |
| 2,247,975 | A | 10/1881 | Wickes |

(Continued)

FOREIGN PATENT DOCUMENTS

| | | | |
|---|---|---|---|
| CN | 1950049 A | 4/2007 | |
| DE | 1913926 A1 | 9/1970 | |

(Continued)

OTHER PUBLICATIONS

Office Action dated Nov. 11, 2013 in IL Application No. 218730.
(Continued)

*Primary Examiner* — Philip R Wiest
(74) *Attorney, Agent, or Firm* — Panitch Schwarze Belisario & Nadel LLP

(57) ABSTRACT

Medical devices including a vial adapter with an inline dry drug module for use with a vial, a needleless syringe and a carrier liquid for filling the needleless syringe with an injection solution for injection to a patient. The inline dry drug modules include a dry drug storage component for storing a dry drug dosage and a uniform carrier liquid distribution component for promoting uniform contact of the dry drug storage component by the carrier liquid to form an injection solution from the dry drug dosage. The inline dry drug modules can include a discrete dry drug storage component and a discrete uniform carrier liquid distribution component or a dual purpose component for both drug storage and uniform carrier liquid distribution. The vial adapters can be provided in vented or non-vented versions.

6 Claims, 6 Drawing Sheets

(52) U.S. Cl.
CPC ....... *A61M 5/284* (2013.01); *A61M 2209/045* (2013.01)

(58) Field of Classification Search
USPC .................................................. 604/403–416
See application file for complete search history.

(56) References Cited

U.S. PATENT DOCUMENTS

| | | | |
|---|---|---|---|
| 254,444 A | 2/1882 | Vogel | |
| 300,060 A | 6/1884 | Ford | |
| 1,021,681 A | 3/1912 | Jennings | |
| 1,704,817 A | 3/1929 | Ayers | |
| 1,930,944 A | 10/1933 | Schmitz, Jr. | |
| 2,326,490 A | 8/1943 | Perelson | |
| 2,560,162 A | 7/1951 | Garwood | |
| 2,748,769 A | 6/1956 | Huber | |
| 2,830,587 A | 4/1958 | Everett | |
| 2,931,668 A | 4/1960 | Baley | |
| 2,968,497 A | 1/1961 | Treleman | |
| 3,059,643 A | 10/1962 | Barton | |
| D198,499 S | 6/1964 | Harautuneian | |
| 3,225,763 A | 12/1965 | Waterman | |
| 3,277,893 A | 10/1966 | Clark | |
| 3,308,822 A | 3/1967 | De Luca | |
| 3,484,849 A | 12/1969 | Huebner et al. | |
| 3,618,637 A | 11/1971 | Santomieri | |
| 3,757,981 A | 9/1973 | Harris, Sr. et al. | |
| 3,788,524 A | 1/1974 | Davis et al. | |
| 3,822,700 A | 7/1974 | Pennington | |
| 3,826,261 A | 7/1974 | Killinger | |
| 3,872,992 A | 3/1975 | Larson | |
| 3,885,607 A | 5/1975 | Peltier | |
| 3,938,520 A | 2/1976 | Scislowicz et al. | |
| 3,957,052 A | 5/1976 | Topham | |
| 3,977,555 A | 8/1976 | Larson | |
| 3,993,063 A | 11/1976 | Larrabee | |
| 4,020,839 A | 5/1977 | Klapp | |
| 4,051,852 A | 10/1977 | Villari | |
| D247,975 S | 5/1978 | Luther | |
| D248,568 S | 7/1978 | Ismach | |
| 4,109,670 A | 8/1978 | Slagel | |
| 4,121,585 A | 10/1978 | Becker, Jr. | |
| 4,161,178 A | 7/1979 | Genese | |
| 4,187,848 A | 2/1980 | Taylor | |
| D254,444 S | 3/1980 | Levine | |
| 4,203,067 A | 5/1980 | Fitzky et al. | |
| 4,203,443 A | 5/1980 | Genese | |
| 4,210,173 A | 7/1980 | Choksi et al. | |
| D257,286 S | 10/1980 | Folkman | |
| 4,253,501 A | 3/1981 | Ogle | |
| 4,296,786 A | 10/1981 | Brignola | |
| 4,303,067 A | 12/1981 | Connolly et al. | |
| 4,312,349 A | 1/1982 | Cohen | |
| 4,314,586 A | 2/1982 | Folkman | |
| 4,328,802 A | 5/1982 | Curley et al. | |
| 4,335,717 A | 6/1982 | Bujan et al. | |
| D267,199 S | 12/1982 | Koenig | |
| 4,376,634 A | 3/1983 | Prior et al. | |
| D268,871 S | 5/1983 | Benham et al. | |
| 4,392,850 A | 7/1983 | Elias et al. | |
| D270,282 S | 8/1983 | Gross | |
| 4,410,321 A | 10/1983 | Pearson et al. | |
| 4,411,662 A | 10/1983 | Pearson | |
| D271,421 S | 11/1983 | Fetterman | |
| 4,434,823 A | 3/1984 | Hudspith | |
| 4,465,471 A | 8/1984 | Harris et al. | |
| 4,475,915 A | 10/1984 | Sloane | |
| 4,493,348 A | 1/1985 | Lemmons | |
| 4,505,709 A | 3/1985 | Froning et al. | |
| 4,507,113 A | 3/1985 | Dunlap | |
| D280,018 S | 8/1985 | Scott | |
| 4,532,969 A | 8/1985 | Kwaan | |
| 4,564,054 A | 1/1986 | Gustavsson | |
| 4,573,993 A | 3/1986 | Hoag et al. | |
| 4,576,211 A | 3/1986 | Valentini et al. | |
| 4,581,014 A | 4/1986 | Millerd et al. | |
| 4,585,446 A | 4/1986 | Kempf | |
| 4,588,396 A | 5/1986 | Stroebel et al. | |
| 4,588,403 A | 5/1986 | Weiss et al. | |
| D284,603 S | 7/1986 | Loignon | |
| 4,604,093 A | 8/1986 | Brown et al. | |
| 4,607,671 A | 8/1986 | Aalto et al. | |
| 4,614,437 A | 9/1986 | Buehler | |
| 4,638,975 A | 1/1987 | Iuchi et al. | |
| 4,639,019 A | 1/1987 | Mittleman | |
| 4,667,927 A | 5/1987 | Oscarsson | |
| 4,675,020 A | 6/1987 | McPhee | |
| 4,676,530 A | 6/1987 | Nordgren et al. | |
| 4,683,975 A | 8/1987 | Booth et al. | |
| 4,697,622 A | 10/1987 | Swift et al. | |
| 4,721,133 A | 1/1988 | Sundblom | |
| 4,729,401 A | 3/1988 | Raines | |
| 4,735,608 A | 4/1988 | Sardam | |
| 4,743,229 A | 5/1988 | Chu | |
| 4,743,243 A | 5/1988 | Vaillancourt | |
| 4,752,292 A | 6/1988 | Lopez et al. | |
| 4,758,235 A | 7/1988 | Tu | |
| 4,759,756 A | 7/1988 | Forman et al. | |
| 4,778,447 A | 10/1988 | Velde et al. | |
| 4,787,898 A | 11/1988 | Raines | |
| 4,797,898 A | 1/1989 | Martinez | |
| D300,060 S | 2/1989 | Molgaard-Nielsen | |
| 4,804,366 A | 2/1989 | Zdeb et al. | |
| 4,826,492 A | 5/1989 | Magasi | |
| 4,832,690 A | 5/1989 | Kuu | |
| 4,834,152 A | 5/1989 | Howson et al. | |
| D303,013 S | 8/1989 | Konopka | |
| 4,857,062 A | 8/1989 | Russell | |
| 4,865,592 A | 9/1989 | Rycroft | |
| 4,871,463 A | 10/1989 | Taylor et al. | |
| 4,898,209 A | 2/1990 | Zbed | |
| 4,909,290 A | 3/1990 | Coccia | |
| 4,927,423 A | 5/1990 | Malmborg | |
| 4,931,040 A | 6/1990 | Haber et al. | |
| 4,932,944 A | 6/1990 | Jagger et al. | |
| 4,967,797 A | 11/1990 | Manska | |
| D314,050 S | 1/1991 | Sone | |
| D314,622 S | 2/1991 | Andersson et al. | |
| 4,997,430 A | 3/1991 | Van der Heiden et al. | |
| 5,006,114 A | 4/1991 | Rogers et al. | |
| 5,035,686 A | 7/1991 | Crittenden et al. | |
| 5,041,105 A | 8/1991 | D'Alo et al. | |
| 5,045,066 A | 9/1991 | Scheuble et al. | |
| 5,049,129 A | 9/1991 | Zdeb et al. | |
| 5,053,015 A | 10/1991 | Gross | |
| 5,061,248 A | 10/1991 | Sacco | |
| 5,088,996 A | 2/1992 | Kopfer et al. | |
| 5,096,575 A | 3/1992 | Cosack | |
| 5,104,387 A | 4/1992 | Pokorney et al. | |
| 5,113,904 A | 5/1992 | Aslanian | |
| 5,122,124 A | 6/1992 | Novacek et al. | |
| 5,125,908 A | 6/1992 | Cohen | |
| 5,125,915 A | 6/1992 | Berry et al. | |
| D328,788 S | 8/1992 | Sagae et al. | |
| 5,171,230 A | 12/1992 | Eland et al. | |
| 5,201,705 A | 4/1993 | Berglund et al. | |
| 5,201,717 A | 4/1993 | Wyatt et al. | |
| 5,203,771 A | 4/1993 | Melker et al. | |
| 5,203,775 A | 4/1993 | Frank et al. | |
| 5,211,638 A | 5/1993 | Dudar et al. | |
| 5,232,029 A | 8/1993 | Knox et al. | |
| 5,232,109 A | 8/1993 | Tirrell et al. | |
| 5,242,432 A | 9/1993 | DeFrank | |
| 5,247,972 A | 9/1993 | Tetreault | |
| D341,420 S | 11/1993 | Conn | |
| 5,269,768 A | 12/1993 | Cheung | |
| 5,270,219 A | 12/1993 | DeCastro et al. | |
| 5,279,576 A | 1/1994 | Loo et al. | |
| 5,288,290 A | 2/1994 | Brody | |
| 5,300,034 A | 4/1994 | Behnke et al. | |
| 5,301,685 A | 4/1994 | Guirguis | |
| 5,304,163 A | 4/1994 | Bonnici et al. | |
| 5,304,165 A | 4/1994 | Haber et al. | |
| 5,308,483 A | 5/1994 | Sklar et al. | |

(56) References Cited

U.S. PATENT DOCUMENTS

| | | |
|---|---|---|
| 5,312,377 A | 5/1994 | Dalton |
| 5,328,474 A | 7/1994 | Raines |
| D349,648 S | 8/1994 | Tirrell et al. |
| 5,334,163 A | 8/1994 | Sinnett |
| 5,334,179 A | 8/1994 | Poli et al. |
| 5,342,346 A | 8/1994 | Honda et al. |
| 5,344,417 A | 9/1994 | Wadsworth, Jr. |
| 5,348,548 A | 9/1994 | Meyer et al. |
| 5,350,372 A | 9/1994 | Ikeda et al. |
| 5,364,386 A | 11/1994 | Fukuoka et al. |
| 5,364,387 A | 11/1994 | Sweeney |
| 5,374,264 A | 12/1994 | Wadsworth, Jr. |
| 5,385,547 A | 1/1995 | Wong et al. |
| 5,397,303 A | 3/1995 | Sancoff et al. |
| D357,733 S | 4/1995 | Matkovich |
| 5,429,614 A | 7/1995 | Fowles et al. |
| 5,433,330 A | 7/1995 | Yatsko et al. |
| 5,445,630 A | 8/1995 | Richmond |
| 5,445,631 A | 8/1995 | Uchida |
| D362,718 S | 9/1995 | Deily et al. |
| 5,451,374 A | 9/1995 | Molina |
| 5,454,805 A | 10/1995 | Brony |
| 5,464,111 A | 11/1995 | Vacek et al. |
| 5,464,123 A | 11/1995 | Scarrow |
| 5,466,219 A | 11/1995 | Lynn et al. |
| 5,466,220 A | 11/1995 | Brenneman |
| 5,470,327 A | 11/1995 | Helgren et al. |
| 5,471,994 A | 12/1995 | Guirguis |
| 5,472,022 A | 12/1995 | Michel et al. |
| 5,478,337 A | 12/1995 | Okamoto et al. |
| 5,492,147 A | 2/1996 | Challender et al. |
| D369,406 S | 4/1996 | Niedospial et al. |
| 5,505,714 A | 4/1996 | Dassa et al. |
| 5,509,433 A | 4/1996 | Paradis |
| 5,515,871 A | 5/1996 | Bittner et al. |
| 5,520,659 A | 5/1996 | Hedges |
| 5,526,853 A | 6/1996 | McPhee et al. |
| 5,527,306 A | 6/1996 | Haining |
| 5,531,695 A | 7/1996 | Swisher |
| 5,547,471 A | 8/1996 | Thompson et al. |
| 5,549,577 A | 8/1996 | Siegel et al. |
| 5,554,128 A | 9/1996 | Hedges |
| 5,562,696 A | 10/1996 | Nobles et al. |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley, III et al. |
| 5,603,706 A | 2/1997 | Wyatt et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,637,101 A | 6/1997 | Shillington |
| 5,641,010 A | 6/1997 | Maier |
| 5,645,538 A | 7/1997 | Richmond |
| 5,647,845 A | 7/1997 | Haber et al. |
| 5,651,776 A | 7/1997 | Appling et al. |
| 5,653,686 A | 8/1997 | Coulter et al. |
| 5,674,195 A | 10/1997 | Truthan |
| 5,676,346 A | 10/1997 | Leinsing |
| 5,685,845 A | 11/1997 | Grimard |
| D388,172 S | 12/1997 | Cipes |
| 5,699,821 A | 12/1997 | Paradis |
| 5,702,019 A | 12/1997 | Grimard |
| 5,718,346 A | 2/1998 | Weiler |
| D393,722 S | 4/1998 | Fangrow, Jr. et al. |
| 5,738,144 A | 4/1998 | Rogers |
| 5,743,312 A | 4/1998 | Pfeifer et al. |
| 5,746,733 A | 5/1998 | Capaccio et al. |
| 5,752,942 A | 5/1998 | Doyle et al. |
| 5,755,696 A | 5/1998 | Caizza |
| 5,766,211 A | 6/1998 | Wood et al. |
| 5,772,630 A | 6/1998 | Ljungquist |
| 5,772,652 A | 6/1998 | Zielinski |
| RE35,841 E | 7/1998 | Frank et al. |
| 5,776,116 A | 7/1998 | Lopez et al. |
| 5,782,872 A | 7/1998 | Muller |
| 5,806,831 A | 9/1998 | Paradis |
| 5,810,792 A | 9/1998 | Fangrow, Jr. et al. |
| D399,559 S | 10/1998 | Molina |
| 5,817,082 A | 10/1998 | Niedospial, Jr. et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,834,744 A | 11/1998 | Risman |
| 5,839,715 A | 11/1998 | Leinsing |
| 5,853,406 A | 12/1998 | Masuda et al. |
| D405,522 S | 2/1999 | Hoenig et al. |
| 5,871,110 A | 2/1999 | Grimard et al. |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,890,610 A | 4/1999 | Jansen et al. |
| 5,891,129 A | 4/1999 | Daubert et al. |
| 5,893,397 A | 4/1999 | Peterson et al. |
| 5,897,526 A | 4/1999 | Vaillancourt |
| 5,899,468 A | 5/1999 | Apps et al. |
| 5,902,280 A | 5/1999 | Powles et al. |
| 5,902,298 A | 5/1999 | Niedospial, Jr. et al. |
| D410,740 S | 6/1999 | Molina |
| 5,911,710 A | 6/1999 | Barry et al. |
| 5,919,182 A | 7/1999 | Avallone |
| 5,921,419 A | 7/1999 | Niedospial, Jr. et al. |
| 5,924,584 A | 7/1999 | Hellstrom et al. |
| 5,925,029 A | 7/1999 | Jansen et al. |
| 5,935,112 A | 8/1999 | Stevens et al. |
| 5,941,848 A | 8/1999 | Nishimoto et al. |
| 5,944,700 A | 8/1999 | Nguyen et al. |
| 5,954,104 A | 9/1999 | Daubert et al. |
| 5,968,022 A | 10/1999 | Saito |
| 5,971,181 A | 10/1999 | Niedospial, Jr. et al. |
| 5,971,965 A | 10/1999 | Mayer |
| 5,989,237 A | 11/1999 | Fowles et al. |
| 6,003,566 A | 12/1999 | Thibault et al. |
| 6,004,278 A | 12/1999 | Botich et al. |
| 6,019,750 A | 2/2000 | Fowles et al. |
| 6,022,339 A | 2/2000 | Fowles et al. |
| 6,036,171 A | 3/2000 | Weinheimer et al. |
| 6,039,093 A | 3/2000 | Mrotzek et al. |
| 6,039,302 A | 3/2000 | Cote, Sr. et al. |
| D422,357 S | 4/2000 | Niedospial, Jr. et al. |
| 6,063,068 A | 5/2000 | Fowles et al. |
| D427,308 S | 6/2000 | Zinger |
| D427,309 S | 6/2000 | Molina |
| 6,070,623 A | 6/2000 | Aneas |
| 6,071,270 A | 6/2000 | Fowles et al. |
| 6,080,132 A | 6/2000 | Cole et al. |
| D428,141 S | 7/2000 | Brotspies et al. |
| 6,086,762 A | 7/2000 | Guala |
| 6,089,541 A | 7/2000 | Weinheimer et al. |
| 6,090,091 A | 7/2000 | Fowles et al. |
| 6,090,093 A | 7/2000 | Thibault et al. |
| 6,092,692 A | 7/2000 | Riskin |
| D430,291 S | 8/2000 | Jansen et al. |
| 6,099,511 A | 8/2000 | Devos et al. |
| 6,113,068 A | 9/2000 | Ryan |
| 6,113,583 A | 9/2000 | Fowles et al. |
| 6,117,114 A | 9/2000 | Paradis |
| D431,864 S | 10/2000 | Jansen |
| 6,139,534 A | 10/2000 | Niedospial, Jr. et al. |
| 6,142,446 A | 11/2000 | Leinsing |
| 6,146,362 A | 11/2000 | Turnbull et al. |
| 6,149,623 A | 11/2000 | Reynolds |
| 6,156,025 A | 12/2000 | Niedospial, Jr. et al. |
| 6,159,192 A | 12/2000 | Fowles et al. |
| 6,168,037 B1 | 1/2001 | Grimard |
| 6,171,287 B1 | 1/2001 | Lynn et al. |
| 6,171,293 B1 | 1/2001 | Rowley et al. |
| 6,173,852 B1 | 1/2001 | Browne |

(56) References Cited

U.S. PATENT DOCUMENTS

| | | |
|---|---|---|
| 6,173,868 B1 | 1/2001 | DeJonge |
| 6,174,304 B1 | 1/2001 | Weston |
| 6,179,822 B1 | 1/2001 | Niedospial, Jr. |
| 6,179,823 B1 | 1/2001 | Niedospial, Jr. |
| 6,206,861 B1 | 3/2001 | Mayer |
| 6,221,041 B1 | 4/2001 | Russo |
| 6,221,054 B1 | 4/2001 | Martin et al. |
| 6,221,065 B1 | 4/2001 | Davis |
| 6,238,372 B1 | 5/2001 | Zinger et al. |
| 6,245,044 B1 | 6/2001 | Daw et al. |
| D445,501 S | 7/2001 | Niedospial, Jr. |
| D445,895 S | 7/2001 | Svendsen |
| 6,253,804 B1 | 7/2001 | Safabash |
| 6,258,078 B1 | 7/2001 | Thilly |
| 6,280,430 B1 | 8/2001 | Neftel et al. |
| 6,290,688 B1 | 9/2001 | Lopez et al. |
| 6,296,621 B1 | 10/2001 | Masuda et al. |
| 6,299,131 B1 | 10/2001 | Ryan |
| 6,343,629 B1 | 2/2002 | Wessman et al. |
| 6,348,044 B1 | 2/2002 | Coletti et al. |
| 6,358,236 B1 | 3/2002 | DeFoggi et al. |
| 6,364,866 B1 | 4/2002 | Furr et al. |
| 6,378,576 B2 | 4/2002 | Thibault et al. |
| 6,378,714 B1 | 4/2002 | Jansen et al. |
| 6,379,340 B1 | 4/2002 | Zinger et al. |
| D457,954 S | 5/2002 | Wallace et al. |
| 6,382,442 B1 | 5/2002 | Thibault et al. |
| 6,386,397 B2 | 5/2002 | Brotspies et al. |
| 6,408,897 B1 | 6/2002 | Laurent et al. |
| 6,409,708 B1 | 6/2002 | Wessman |
| 6,440,107 B1 | 8/2002 | Trombley, III et al. |
| 6,453,949 B1 | 9/2002 | Chau |
| 6,453,956 B2 | 9/2002 | Safabash |
| 6,474,375 B2 | 11/2002 | Spero et al. |
| 6,478,788 B1 | 11/2002 | Aneas |
| D468,015 S | 12/2002 | Horppu |
| 6,499,617 B1 | 12/2002 | Niedospial, Jr. |
| 6,503,240 B1 | 1/2003 | Niedospial, Jr. et al. |
| 6,503,244 B2 | 1/2003 | Hayman |
| 6,520,932 B2 | 2/2003 | Taylor |
| 6,524,278 B1 | 2/2003 | Campbell et al. |
| 6,524,295 B2 | 2/2003 | Daubert et al. |
| D472,316 S | 3/2003 | Douglas et al. |
| 6,530,903 B2 | 3/2003 | Wang et al. |
| 6,537,263 B1 | 3/2003 | Aneas |
| D472,630 S | 4/2003 | Douglas et al. |
| 6,544,246 B1 | 4/2003 | Niedospial, Jr. |
| 6,551,299 B2 | 4/2003 | Miyoshi et al. |
| 6,558,365 B2 | 5/2003 | Zinger et al. |
| 6,571,837 B2 | 6/2003 | Jansen et al. |
| 6,572,591 B2 | 6/2003 | Mayer |
| 6,575,955 B2 | 6/2003 | Azzolini |
| 6,581,593 B1 | 6/2003 | Rubin et al. |
| 6,582,415 B1 | 6/2003 | Fowles et al. |
| D476,731 S | 7/2003 | Cise et al. |
| 6,591,876 B2 | 7/2003 | Safabash |
| 6,599,273 B1 | 7/2003 | Lopez |
| 6,601,721 B2 | 8/2003 | Jansen et al. |
| 6,626,309 B1 | 9/2003 | Jansen et al. |
| 6,638,244 B1 | 10/2003 | Reynolds |
| D482,121 S | 11/2003 | Harding et al. |
| D482,447 S | 11/2003 | Harding et al. |
| 6,651,956 B2 | 11/2003 | Miller |
| 6,652,509 B1 | 11/2003 | Helgren et al. |
| D483,487 S | 12/2003 | Harding et al. |
| D483,869 S | 12/2003 | Tran et al. |
| 6,656,433 B2 | 12/2003 | Sasso |
| 6,666,852 B2 | 12/2003 | Niedospial, Jr. |
| 6,681,810 B2 | 1/2004 | Weston |
| 6,681,946 B1 | 1/2004 | Jansen et al. |
| 6,682,509 B2 | 1/2004 | Lopez |
| 6,692,478 B1 | 2/2004 | Paradis |
| 6,692,829 B2 | 2/2004 | Stubler et al. |
| 6,695,829 B2 | 2/2004 | Hellstrom et al. |
| 6,699,229 B2 | 3/2004 | Zinger et al. |
| 6,706,022 B1 | 3/2004 | Leinsing et al. |
| 6,706,031 B2 | 3/2004 | Manera |
| 6,715,520 B2 | 4/2004 | Andreasson et al. |
| 6,729,370 B2 | 5/2004 | Norton et al. |
| 6,736,798 B2 | 5/2004 | Ohkubo et al. |
| 6,745,998 B2 | 6/2004 | Doyle |
| 6,746,438 B1 | 6/2004 | Amissolle |
| 6,752,180 B2 | 6/2004 | Delay |
| D495,416 S | 8/2004 | Dimeo et al. |
| D496,457 S | 9/2004 | Prais et al. |
| 6,802,490 B2 | 10/2004 | Leinsing et al. |
| 6,832,994 B2 | 12/2004 | Niedospial, Jr. et al. |
| 6,852,103 B2 | 2/2005 | Fowles et al. |
| 6,875,203 B1 | 4/2005 | Fowles et al. |
| 6,875,205 B2 | 4/2005 | Leinsing |
| 6,878,131 B2 | 4/2005 | Novacek et al. |
| 6,884,253 B1 | 4/2005 | McFarlane |
| 6,890,328 B2 | 5/2005 | Fowles et al. |
| D506,256 S | 6/2005 | Miyoshi et al. |
| 6,901,975 B2 | 6/2005 | Aramata et al. |
| 6,945,417 B2 | 9/2005 | Jansen et al. |
| 6,948,522 B2 | 9/2005 | Newbrough et al. |
| 6,949,086 B2 | 9/2005 | Ferguson et al. |
| 6,951,613 B2 | 10/2005 | Reif et al. |
| 6,957,745 B2 | 10/2005 | Thibault et al. |
| 6,960,164 B2 | 11/2005 | O'Heeron |
| 6,979,318 B1 | 12/2005 | McDonald et al. |
| RE38,996 E | 2/2006 | Crawford et al. |
| 6,994,315 B2 | 2/2006 | Ryan et al. |
| 6,997,916 B2 | 2/2006 | Simas, Jr. et al. |
| 6,997,917 B2 | 2/2006 | Niedospial, Jr. et al. |
| 7,024,968 B2 | 4/2006 | Raudabough et al. |
| 7,070,589 B2 | 7/2006 | Lolachi et al. |
| 7,074,216 B2 | 7/2006 | Fowles et al. |
| 7,083,600 B2 | 8/2006 | Meloul |
| 7,086,431 B2 | 8/2006 | D'Antonio et al. |
| 7,100,890 B2 | 9/2006 | Cote, Sr. et al. |
| 7,140,401 B2 | 11/2006 | Wilcox et al. |
| 7,150,735 B2 | 12/2006 | Hickle |
| 7,192,423 B2 | 3/2007 | Wong |
| 7,195,623 B2 | 3/2007 | Burroughs et al. |
| 7,241,285 B1 | 7/2007 | Dikeman |
| 7,294,122 B2 | 11/2007 | Kubo et al. |
| 7,306,199 B2 | 12/2007 | Leinsing et al. |
| D561,348 S | 2/2008 | Zinger et al. |
| 7,326,188 B1 | 2/2008 | Russell et al. |
| 7,326,194 B2 | 2/2008 | Zinger et al. |
| 7,350,764 B2 | 4/2008 | Raybuck |
| 7,354,422 B2 | 4/2008 | Riesenberger et al. |
| 7,354,427 B2 | 4/2008 | Fangrow |
| 7,425,209 B2 | 9/2008 | Fowles et al. |
| 7,435,246 B2 | 10/2008 | Zihlmann |
| D580,558 S | 11/2008 | Shigesada et al. |
| 7,452,348 B2 | 11/2008 | Hasegawa |
| 7,470,257 B2 | 12/2008 | Norton et al. |
| 7,470,265 B2 | 12/2008 | Brugger et al. |
| 7,472,932 B2 | 1/2009 | Weber et al. |
| 7,488,297 B2 | 2/2009 | Flaherty |
| 7,491,197 B2 | 2/2009 | Jansen et al. |
| 7,497,848 B2 | 3/2009 | Leinsing et al. |
| 7,523,967 B2 | 4/2009 | Steppe |
| 7,530,546 B2 | 5/2009 | Ryan et al. |
| D595,420 S | 6/2009 | Suzuki et al. |
| D595,421 S | 6/2009 | Suzuki et al. |
| 7,540,863 B2 | 6/2009 | Haindl |
| 7,540,865 B2 | 6/2009 | Griffin et al. |
| 7,544,191 B2 | 6/2009 | Peluso et al. |
| D595,862 S | 7/2009 | Suzuki et al. |
| D595,863 S | 7/2009 | Suzuki et al. |
| 7,611,487 B2 | 11/2009 | Woehr et al. |
| 7,611,502 B2 | 11/2009 | Daly |
| 7,615,041 B2 | 11/2009 | Sullivan et al. |
| 7,628,779 B2 | 12/2009 | Aneas |
| 7,632,261 B2 | 12/2009 | Zinger et al. |
| D608,900 S | 1/2010 | Giraud et al. |
| 7,654,995 B2 | 2/2010 | Warren et al. |
| 7,670,326 B2 | 3/2010 | Shemesh |
| 7,695,445 B2 | 4/2010 | Yuki |
| D616,090 S | 5/2010 | Kawamura |

(56) References Cited

U.S. PATENT DOCUMENTS

| | | | |
|---|---|---|---|
| 7,713,247 B2 | 5/2010 | Lopez | |
| 7,717,886 B2 | 5/2010 | Lopez | |
| 7,722,090 B2 | 5/2010 | Burton et al. | |
| D616,984 S | 6/2010 | Gilboa | |
| 7,731,678 B2 | 6/2010 | Tennican et al. | |
| 7,743,799 B2 | 6/2010 | Mosler et al. | |
| 7,744,581 B2 | 6/2010 | Wallen et al. | |
| 7,757,901 B2 | 7/2010 | Welp | |
| 7,758,082 B2 | 7/2010 | Weigel et al. | |
| 7,758,560 B2 | 7/2010 | Connell et al. | |
| 7,762,524 B2 | 7/2010 | Cawthon et al. | |
| 7,766,304 B2 | 8/2010 | Phillips | |
| 7,771,383 B2 | 8/2010 | Truitt et al. | |
| D624,641 S | 9/2010 | Boclet | |
| 7,799,009 B2 | 9/2010 | Niedospial, Jr. et al. | |
| 7,803,140 B2 | 9/2010 | Fangrow, Jr. | |
| D627,216 S | 11/2010 | Fulginiti | |
| D630,732 S | 1/2011 | Lev et al. | |
| 7,862,537 B2 | 1/2011 | Zinger et al. | |
| 7,867,215 B2 | 1/2011 | Akerlund et al. | |
| 7,879,018 B2 | 2/2011 | Zinger et al. | |
| 7,895,216 B2 | 2/2011 | Longshaw et al. | |
| D634,007 S | 3/2011 | Zinger et al. | |
| 7,900,659 B2 | 3/2011 | Whitley et al. | |
| D637,713 S | 5/2011 | Nord et al. | |
| D641,080 S | 7/2011 | Zinger et al. | |
| 7,985,216 B2 | 7/2011 | Daily et al. | |
| D644,104 S | 8/2011 | Maeda et al. | |
| 7,993,328 B2 | 8/2011 | Whitley | |
| 8,007,461 B2 | 8/2011 | Huo et al. | |
| 8,012,132 B2 | 9/2011 | Lum et al. | |
| 8,016,809 B2 | 9/2011 | Zinger et al. | |
| 8,021,325 B2 | 9/2011 | Zinger et al. | |
| 8,025,653 B2 | 9/2011 | Capitaine et al. | |
| 8,029,472 B2 | 10/2011 | Leinsing et al. | |
| 8,038,123 B2 | 10/2011 | Ruschke et al. | |
| 8,066,688 B2 | 11/2011 | Zinger et al. | |
| 8,070,739 B2 | 12/2011 | Zinger et al. | |
| 8,075,550 B2 | 12/2011 | Nord et al. | |
| 8,096,525 B2 | 1/2012 | Ryan | |
| 8,105,314 B2 | 1/2012 | Fangrow, Jr. | |
| D654,166 S | 2/2012 | Lair | |
| D655,017 S | 2/2012 | Mosler et al. | |
| 8,122,923 B2 | 2/2012 | Kraus et al. | |
| 8,123,736 B2 | 2/2012 | Kraushaar et al. | |
| D657,461 S | 4/2012 | Schembre et al. | |
| 8,157,784 B2 | 4/2012 | Rogers | |
| 8,167,863 B2 | 5/2012 | Yow | |
| 8,172,824 B2 | 5/2012 | Pfeifer et al. | |
| 8,177,768 B2 | 5/2012 | Leinsing | |
| 8,182,452 B2 | 5/2012 | Mansour et al. | |
| 8,187,248 B2 | 5/2012 | Zihlmann | |
| 8,196,614 B2 | 6/2012 | Kriheli | |
| 8,197,459 B2 | 6/2012 | Jansen et al. | |
| 8,211,069 B2 | 7/2012 | Fangrow, Jr. | |
| 8,225,959 B2 | 7/2012 | Lambrecht | |
| 8,241,268 B2 | 8/2012 | Whitley | |
| 8,262,628 B2 | 9/2012 | Fangrow, Jr. | |
| 8,262,641 B2 | 9/2012 | Vedrine et al. | |
| 8,267,127 B2 | 9/2012 | Kriheli | |
| D669,980 S | 10/2012 | Lev et al. | |
| 8,287,513 B2 | 10/2012 | Ellstrom et al. | |
| 8,328,784 B2 * | 12/2012 | Jensen | A61J 1/10 210/646 |
| D673,673 S | 1/2013 | Wang | |
| D674,084 S | 1/2013 | Linnenschmidt | |
| D674,088 S | 1/2013 | Lev et al. | |
| D681,230 S | 4/2013 | Mosler et al. | |
| 8,454,573 B2 | 6/2013 | Wyatt et al. | |
| 8,469,939 B2 | 6/2013 | Fangrow, Jr. | |
| 8,475,404 B2 | 7/2013 | Foshee et al. | |
| 8,480,645 B1 | 7/2013 | Choudhury et al. | |
| 8,480,646 B2 | 7/2013 | Nord et al. | |
| 8,506,548 B2 | 8/2013 | Okiyama | |
| 8,511,352 B2 | 8/2013 | Kraus et al. | |
| 8,512,309 B2 | 8/2013 | Shemesh et al. | |
| D690,009 S | 9/2013 | Schembre et al. | |
| D690,418 S | 9/2013 | Rosenquist | |
| 8,523,837 B2 | 9/2013 | Wiggins et al. | |
| 8,545,476 B2 | 10/2013 | Ariagno et al. | |
| 8,551,067 B2 | 10/2013 | Zinger et al. | |
| 8,556,879 B2 | 10/2013 | Okiyama | |
| 8,562,582 B2 | 10/2013 | Tuckwell et al. | |
| 8,608,723 B2 | 12/2013 | Lev et al. | |
| 8,628,508 B2 | 1/2014 | Weitzel et al. | |
| 8,684,992 B2 | 4/2014 | Sullivan et al. | |
| 8,752,598 B2 | 6/2014 | Denenburg et al. | |
| D714,935 S | 10/2014 | Nishioka et al. | |
| D717,406 S | 11/2014 | Stanley et al. | |
| D717,948 S | 11/2014 | Strong et al. | |
| D719,650 S | 12/2014 | Arinobe et al. | |
| D720,067 S | 12/2014 | Rosenquist | |
| D720,451 S | 12/2014 | Denenburg et al. | |
| D720,452 S | 12/2014 | Jordan | |
| 8,900,212 B2 | 12/2014 | Kubo | |
| D720,850 S | 1/2015 | Hsia et al. | |
| D732,660 S | 6/2015 | Ohashi | |
| D732,664 S | 6/2015 | Woehr et al. | |
| D733,291 S | 6/2015 | Wang | |
| D733,292 S | 6/2015 | Rogers | |
| D733,293 S | 6/2015 | Rogers | |
| D738,494 S | 9/2015 | Kashmirian | |
| D741,457 S | 10/2015 | Guest | |
| D750,235 S | 2/2016 | Maurice | |
| 2001/0000347 A1 | 4/2001 | Hellstrom et al. | |
| 2001/0025671 A1 | 10/2001 | Safabash | |
| 2001/0029360 A1 | 10/2001 | Miyoshi et al. | |
| 2001/0051793 A1 | 12/2001 | Weston | |
| 2002/0017328 A1 | 2/2002 | Loo | |
| 2002/0066715 A1 | 6/2002 | Niedospial | |
| 2002/0087118 A1 | 7/2002 | Reynolds et al. | |
| 2002/0087141 A1 | 7/2002 | Zinger et al. | |
| 2002/0087144 A1 | 7/2002 | Zinger et al. | |
| 2002/0121496 A1 | 9/2002 | Thiebault et al. | |
| 2002/0123736 A1 | 9/2002 | Fowles et al. | |
| 2002/0127150 A1 | 9/2002 | Sasso | |
| 2002/0128628 A1 | 9/2002 | Fathallah | |
| 2002/0138045 A1 | 9/2002 | Moen | |
| 2002/0173752 A1 | 11/2002 | Polzin | |
| 2002/0193777 A1 | 12/2002 | Aneas | |
| 2003/0028156 A1 | 2/2003 | Juliar | |
| 2003/0036725 A1 | 2/2003 | Lavi et al. | |
| 2003/0068354 A1 | 4/2003 | Reif et al. | |
| 2003/0069550 A1 | 4/2003 | Sharp | |
| 2003/0073971 A1 | 4/2003 | Saker | |
| 2003/0100866 A1 | 5/2003 | Reynolds | |
| 2003/0109846 A1 | 6/2003 | Zinger et al. | |
| 2003/0120209 A1 | 6/2003 | Jensen et al. | |
| 2003/0153895 A1 | 8/2003 | Leinsing | |
| 2003/0187420 A1 | 10/2003 | Akerlund et al. | |
| 2003/0191445 A1 | 10/2003 | Wallen et al. | |
| 2003/0195479 A1 | 10/2003 | Kuracina et al. | |
| 2003/0199846 A1 | 10/2003 | Fowles et al. | |
| 2003/0199847 A1 | 10/2003 | Akerlund et al. | |
| 2003/0205843 A1 | 11/2003 | Adams | |
| 2003/0236543 A1 | 12/2003 | Brenneman et al. | |
| 2004/0024354 A1 | 2/2004 | Reynolds | |
| 2004/0039365 A1 | 2/2004 | Aramata et al. | |
| 2004/0044327 A1 | 3/2004 | Hasegawa | |
| 2004/0073189 A1 | 4/2004 | Wyatt et al. | |
| 2004/0143218 A1 | 7/2004 | Das | |
| 2004/0143226 A1 | 7/2004 | Marsden | |
| 2004/0153047 A1 | 8/2004 | Blank et al. | |
| 2004/0162540 A1 | 8/2004 | Walenciak et al. | |
| 2004/0167472 A1 | 8/2004 | Howell et al. | |
| 2004/0181192 A1 | 9/2004 | Cuppy | |
| 2004/0204699 A1 | 10/2004 | Hanly et al. | |
| 2004/0217315 A1 | 11/2004 | Doyle | |
| 2004/0225274 A1 | 11/2004 | Jansen et al. | |
| 2004/0236305 A1 | 11/2004 | Jansen et al. | |
| 2004/0249341 A1 | 12/2004 | Newbrough et al. | |
| 2004/0255952 A1 | 12/2004 | Carlsen et al. | |
| 2005/0015070 A1 | 1/2005 | Delnevo et al. | |
| 2005/0016626 A1 | 1/2005 | Wilcox et al. | |

(56) References Cited

U.S. PATENT DOCUMENTS

| | | |
|---|---|---|
| 2005/0055008 A1 | 3/2005 | Paradis et al. |
| 2005/0082828 A1 | 4/2005 | Wicks et al. |
| 2005/0124964 A1 | 6/2005 | Niedospial et al. |
| 2005/0137523 A1 | 6/2005 | Wyatt et al. |
| 2005/0137566 A1 | 6/2005 | Fowles et al. |
| 2005/0148994 A1 | 7/2005 | Leinsing |
| 2005/0159724 A1 | 7/2005 | Enerson |
| 2005/0182383 A1 | 8/2005 | Wallen |
| 2005/0209554 A1 | 9/2005 | Landau |
| 2005/0261637 A1 | 11/2005 | Miller |
| 2005/0277896 A1 | 12/2005 | Messerli et al. |
| 2006/0030832 A1 | 2/2006 | Niedospial et al. |
| 2006/0079834 A1 | 4/2006 | Tennican et al. |
| 2006/0089594 A1 | 4/2006 | Landau |
| 2006/0089603 A1 | 4/2006 | Truitt et al. |
| 2006/0095015 A1 | 5/2006 | Hobbs et al. |
| 2006/0106360 A1 | 5/2006 | Wong |
| 2006/0135948 A1 | 6/2006 | Varma |
| 2006/0155257 A1 | 7/2006 | Reynolds |
| 2006/0161192 A1 | 7/2006 | Young |
| 2006/0178646 A1 | 8/2006 | Harris et al. |
| 2006/0212004 A1 | 9/2006 | Atil |
| 2006/0253084 A1 | 11/2006 | Nordgren |
| 2006/0259004 A1 | 11/2006 | Connell et al. |
| 2007/0024995 A1 | 2/2007 | Hayashi |
| 2007/0060904 A1 | 3/2007 | Vedrine et al. |
| 2007/0078428 A1 | 4/2007 | Reynolds et al. |
| 2007/0079894 A1 | 4/2007 | Kraus et al. |
| 2007/0083164 A1 | 4/2007 | Barrelle et al. |
| 2007/0088252 A1 | 4/2007 | Pestotnik et al. |
| 2007/0088293 A1 | 4/2007 | Fangrow |
| 2007/0088313 A1 | 4/2007 | Zinger et al. |
| 2007/0106244 A1 | 5/2007 | Mosler et al. |
| 2007/0112324 A1 | 5/2007 | Hamedi-Sangsari |
| 2007/0156112 A1 | 7/2007 | Walsh |
| 2007/0167904 A1 | 7/2007 | Zinger et al. |
| 2007/0191760 A1 | 8/2007 | Iguchi et al. |
| 2007/0191764 A1 | 8/2007 | Zihlmann |
| 2007/0191767 A1 | 8/2007 | Hennessy et al. |
| 2007/0203451 A1 | 8/2007 | Murakami et al. |
| 2007/0219483 A1 | 9/2007 | Kitani et al. |
| 2007/0244447 A1 | 10/2007 | Capitaine et al. |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0249995 A1 | 10/2007 | Van Manen |
| 2007/0255202 A1 | 11/2007 | Kitani et al. |
| 2007/0265574 A1 | 11/2007 | Tennican et al. |
| 2007/0265581 A1 | 11/2007 | Funamura et al. |
| 2007/0270778 A9 | 11/2007 | Zinger et al. |
| 2007/0287953 A1 | 12/2007 | Ziv et al. |
| 2007/0299404 A1 | 12/2007 | Katoh et al. |
| 2008/0009789 A1 | 1/2008 | Zinger et al. |
| 2008/0009822 A1 | 1/2008 | Enerson |
| 2008/0015496 A1 | 1/2008 | Hamedi-Sangsari |
| 2008/0135051 A1 | 6/2008 | Lee |
| 2008/0172024 A1 | 7/2008 | Yow |
| 2008/0188799 A1 | 8/2008 | Mueller-Beckhaus et al. |
| 2008/0249479 A1 | 10/2008 | Zinger et al. |
| 2008/0249498 A1 | 10/2008 | Fangrow |
| 2008/0262465 A1 | 10/2008 | Zinger et al. |
| 2008/0287905 A1 | 11/2008 | Hiejima et al. |
| 2008/0294100 A1 | 11/2008 | de Costa et al. |
| 2008/0306439 A1 | 12/2008 | Nelson et al. |
| 2008/0312634 A1 | 12/2008 | Helmerson et al. |
| 2009/0012492 A1 | 1/2009 | Zihlmann |
| 2009/0082750 A1 | 3/2009 | Denenburg et al. |
| 2009/0143758 A1 | 6/2009 | Okiyama |
| 2009/0177177 A1 | 7/2009 | Zinger et al. |
| 2009/0177178 A1 | 7/2009 | Pedersen |
| 2009/0187140 A1 | 7/2009 | Racz |
| 2009/0216212 A1 | 8/2009 | Fangrow, Jr. |
| 2009/0267011 A1 | 10/2009 | Hatton et al. |
| 2009/0299325 A1 | 12/2009 | Vedrine et al. |
| 2009/0318946 A1 | 12/2009 | Tamesada |
| 2009/0326506 A1 | 12/2009 | Hasegawa et al. |
| 2010/0010443 A1 | 1/2010 | Morgan et al. |
| 2010/0016811 A1 | 1/2010 | Smith |
| 2010/0022985 A1 | 1/2010 | Sullivan et al. |
| 2010/0030181 A1 | 2/2010 | Helle et al. |
| 2010/0036319 A1 | 2/2010 | Drake et al. |
| 2010/0076397 A1 | 3/2010 | Reed et al. |
| 2010/0087786 A1 | 4/2010 | Zinger et al. |
| 2010/0137827 A1 | 6/2010 | Warren et al. |
| 2010/0160889 A1 | 6/2010 | Smith et al. |
| 2010/0168664 A1 | 7/2010 | Zinger et al. |
| 2010/0168712 A1 | 7/2010 | Tuckwell et al. |
| 2010/0179506 A1 | 7/2010 | Shemesh et al. |
| 2010/0198148 A1 | 8/2010 | Zinger et al. |
| 2010/0204670 A1 | 8/2010 | Kraushaar et al. |
| 2010/0241088 A1 | 9/2010 | Ranalletta et al. |
| 2010/0274184 A1 | 10/2010 | Chun |
| 2010/0286661 A1 | 11/2010 | Raday et al. |
| 2010/0312220 A1 | 12/2010 | Kalitzki |
| 2011/0004143 A1 | 1/2011 | Beiriger et al. |
| 2011/0004184 A1 | 1/2011 | Proksch et al. |
| 2011/0044850 A1 | 2/2011 | Solomon et al. |
| 2011/0054440 A1 | 3/2011 | Lewis |
| 2011/0087164 A1 | 4/2011 | Mosler et al. |
| 2011/0160701 A1 | 6/2011 | Wyatt et al. |
| 2011/0172636 A1 | 7/2011 | Aasmul |
| 2011/0175347 A1 | 7/2011 | Okiyama |
| 2011/0218511 A1 | 9/2011 | Yokoyama |
| 2011/0224640 A1 | 9/2011 | Kuhn et al. |
| 2011/0230856 A1 | 9/2011 | Kyle et al. |
| 2011/0264037 A1 | 10/2011 | Foshee et al. |
| 2011/0264069 A1 | 10/2011 | Bochenko |
| 2011/0276007 A1 | 11/2011 | Denenburg |
| 2011/0319827 A1 | 12/2011 | Leinsing et al. |
| 2012/0022469 A1 | 1/2012 | Alpert |
| 2012/0053555 A1 | 3/2012 | Ariagno et al. |
| 2012/0059346 A1 | 3/2012 | Sheppard et al. |
| 2012/0067429 A1 | 3/2012 | Mosler et al. |
| 2012/0078214 A1 | 3/2012 | Finke et al. |
| 2012/0123382 A1 | 5/2012 | Kubo |
| 2012/0184938 A1 | 7/2012 | Lev et al. |
| 2012/0215182 A1 | 8/2012 | Mansour et al. |
| 2012/0220977 A1 | 8/2012 | Yow |
| 2012/0220978 A1 | 8/2012 | Lev et al. |
| 2012/0265163 A1 | 10/2012 | Cheng et al. |
| 2012/0271229 A1 | 10/2012 | Lev et al. |
| 2012/0296307 A1 | 11/2012 | Holt et al. |
| 2012/0310203 A1 | 12/2012 | Khaled et al. |
| 2012/0323172 A1 | 12/2012 | Lev et al. |
| 2012/0323187 A1 | 12/2012 | Iwase et al. |
| 2012/0323210 A1 | 12/2012 | Lev et al. |
| 2013/0046269 A1 | 2/2013 | Lev et al. |
| 2013/0053814 A1 | 2/2013 | Mueller-Beckhaus et al. |
| 2013/0096493 A1 | 4/2013 | Kubo et al. |
| 2013/0144248 A1 | 6/2013 | Putter et al. |
| 2013/0199669 A1 | 8/2013 | Moy et al. |
| 2013/0226100 A1 | 8/2013 | Lev |
| 2013/0231630 A1 | 9/2013 | Kraus et al. |
| 2013/0237904 A1 | 9/2013 | Deneburg et al. |
| 2013/0253448 A1 | 9/2013 | Baron et al. |
| 2013/0289530 A1 | 10/2013 | Wyatt et al. |
| 2014/0020793 A1 | 1/2014 | Denenburg et al. |
| 2014/0096862 A1 | 4/2014 | Aneas |
| 2014/0150911 A1 | 6/2014 | Hanner et al. |
| 2014/0221940 A1 | 8/2014 | Clauson et al. |
| 2014/0277052 A1 | 9/2014 | Haselby et al. |
| 2014/0352845 A1 | 12/2014 | Lev et al. |
| 2015/0082746 A1 | 3/2015 | Ivosevic et al. |
| 2015/0088078 A1 | 3/2015 | Lev et al. |
| 2015/0290390 A1 | 10/2015 | Ring et al. |
| 2015/0305770 A1 | 10/2015 | Fill et al. |
| 2016/0088995 A1 | 3/2016 | Ueda et al. |

FOREIGN PATENT DOCUMENTS

| | | |
|---|---|---|
| DE | 4122476 A1 | 1/1993 |
| DE | 19504413 A1 | 8/1996 |
| DE | 202004012714 U1 | 11/2004 |
| DE | 202009011019 U1 | 12/2010 |

(56) References Cited

FOREIGN PATENT DOCUMENTS

| | | |
|---|---|---|
| EP | 0192661 A1 | 9/1986 |
| EP | 0195018 A1 | 9/1986 |
| EP | 0258913 A2 | 3/1988 |
| EP | 0416454 A2 | 3/1991 |
| EP | 0282545 B1 | 2/1992 |
| EP | 0518397 A1 | 12/1992 |
| EP | 0521460 A1 | 1/1993 |
| EP | 0598918 A1 | 6/1994 |
| EP | 0637443 A1 | 2/1995 |
| EP | 0737467 A1 | 10/1996 |
| EP | 761562 A1 | 3/1997 |
| EP | 765652 A1 | 4/1997 |
| EP | 765853 A1 | 4/1997 |
| EP | 0806597 A1 | 11/1997 |
| EP | 0814866 A1 | 1/1998 |
| EP | 829248 A2 | 3/1998 |
| EP | 0856331 A1 | 8/1998 |
| EP | 882441 A2 | 12/1998 |
| EP | 0887085 A2 | 12/1998 |
| EP | 897708 A2 | 2/1999 |
| EP | 0898951 A2 | 3/1999 |
| EP | 960616 A2 | 12/1999 |
| EP | 1008337 A1 | 6/2000 |
| EP | 1029526 A1 | 8/2000 |
| EP | 1034809 A1 | 9/2000 |
| EP | 1051988 A2 | 11/2000 |
| EP | 1323403 A1 | 7/2003 |
| EP | 1329210 A1 | 7/2003 |
| EP | 1396250 A1 | 3/2004 |
| EP | 1454609 A1 | 9/2004 |
| EP | 1454650 A1 | 9/2004 |
| EP | 1498097 A2 | 1/2005 |
| EP | 1872824 A1 | 1/2008 |
| EP | 1911432 A1 | 4/2008 |
| EP | 1919432 A1 | 5/2008 |
| EP | 1930038 A2 | 6/2008 |
| EP | 2090278 A1 | 8/2009 |
| EP | 2351548 A1 | 8/2011 |
| EP | 2351549 A1 | 8/2011 |
| EP | 2462913 A1 | 6/2012 |
| EP | 2512399 A1 | 10/2012 |
| FR | 2029242 A5 | 10/1970 |
| FR | 2856660 A1 | 12/2004 |
| FR | 2869795 A1 | 11/2005 |
| FR | 2931363 A1 | 11/2009 |
| GB | 1444210 A | 7/1976 |
| IL | 171662 | 10/2005 |
| JP | 03-062426 B | 9/1991 |
| JP | 4329954 A | 11/1992 |
| JP | 06-050656 U | 7/1994 |
| JP | H08-000710 A | 1/1996 |
| JP | 09-104460 A | 4/1997 |
| JP | 09-104461 A | 4/1997 |
| JP | 10-118158 A | 5/1998 |
| JP | H10-504736 A | 5/1998 |
| JP | 11503627 T | 3/1999 |
| JP | 11-319031 A | 11/1999 |
| JP | 2000-508934 A | 7/2000 |
| JP | 2000-237278 A | 9/2000 |
| JP | 2000262497 A | 9/2000 |
| JP | 2001-505083 A | 4/2001 |
| JP | 2002-035140 A | 2/2002 |
| JP | 2002-516160 A | 6/2002 |
| JP | 2002-355318 A | 12/2002 |
| JP | 2003-033441 A | 2/2003 |
| JP | 2003-102807 A | 4/2003 |
| JP | 2004-097253 A | 4/2004 |
| JP | 2004-522541 A | 7/2004 |
| JP | 200661421 A | 3/2006 |
| JP | 2010-179128 A | 8/2010 |
| JP | 2012-205769 A | 10/2012 |
| WO | 8601712 A1 | 3/1986 |
| WO | 8605683 A1 | 10/1986 |
| WO | 9003536 A1 | 4/1990 |
| WO | 9403373 A1 | 2/1994 |
| WO | 9507066 A1 | 3/1995 |
| WO | 9600053 A1 | 1/1996 |
| WO | 9629113 A1 | 9/1996 |
| WO | 9736636 A1 | 10/1997 |
| WO | 9832411 A1 | 7/1998 |
| WO | 9837854 A1 | 9/1998 |
| WO | 9961093 A1 | 12/1999 |
| WO | 0128490 A1 | 4/2001 |
| WO | 0130425 A1 | 5/2001 |
| WO | 0132524 A1 | 5/2001 |
| WO | 0160311 A1 | 8/2001 |
| WO | 0191693 A2 | 12/2001 |
| WO | 200209797 A1 | 2/2002 |
| WO | 0232372 A1 | 4/2002 |
| WO | 0236191 A2 | 5/2002 |
| WO | 02066100 A2 | 8/2002 |
| WO | 02089900 A1 | 11/2002 |
| WO | 03051423 A2 | 6/2003 |
| WO | 03070147 A2 | 8/2003 |
| WO | 03079956 A1 | 10/2003 |
| WO | 2004041148 A1 | 5/2004 |
| WO | 2005002492 A1 | 1/2005 |
| WO | 2005041846 A2 | 5/2005 |
| WO | 2005105014 A2 | 11/2005 |
| WO | 2006099441 A2 | 9/2006 |
| WO | 2007015233 A1 | 2/2007 |
| WO | 2007017868 A1 | 2/2007 |
| WO | 2007052252 A1 | 5/2007 |
| WO | 2007101772 A1 | 9/2007 |
| WO | 2007105221 A1 | 9/2007 |
| WO | WO 2007/101772 * 9/2007 ................ A61J 1/00 |
| WO | 2008081424 A2 | 7/2008 |
| WO | 2008126090 A1 | 10/2008 |
| WO | 2009026443 A2 | 2/2009 |
| WO | 2009029010 A1 | 3/2009 |
| WO | 2009038860 A2 | 3/2009 |
| WO | 2009040804 A2 | 4/2009 |
| WO | 2009087572 A1 | 7/2009 |
| WO | 2009093249 A1 | 7/2009 |
| WO | 2009112489 A1 | 9/2009 |
| WO | 2009146088 A1 | 12/2009 |
| WO | 2010061743 A1 | 6/2010 |
| WO | 2010117580 A1 | 10/2010 |
| WO | 2011004360 A1 | 1/2011 |
| WO | 2011039747 A1 | 4/2011 |
| WO | 2011058545 A1 | 5/2011 |
| WO | 2011058548 A1 | 5/2011 |
| WO | 2011077434 A1 | 6/2011 |
| WO | 2011104711 A1 | 9/2011 |
| WO | 2012004784 A1 | 1/2012 |
| WO | 2012063230 A1 | 5/2012 |
| WO | 2012143921 A1 | 10/2012 |
| WO | 2012150587 A1 | 11/2012 |
| WO | 2013127813 A1 | 9/2013 |
| WO | 2013134246 A1 | 9/2013 |
| WO | 2013156944 A1 | 10/2013 |
| WO | 2013156994 A1 | 10/2013 |
| WO | 2014033706 A2 | 3/2014 |
| WO | 2014033710 A1 | 3/2014 |
| WO | 2014174278 A1 | 10/2014 |
| WO | 2016023590 A1 | 2/2016 |

OTHER PUBLICATIONS

U.S. Appl. No. 29/478,723, Lev, filed Jan. 8, 2014.
U.S. Appl. No. 29/478,726, Lev, filed Jan. 8, 2014.
Office Action dated Jan. 2, 2014 in U.S. Appl. No. 13/505,881, Lev.
Int'l Preliminary Report on Patentability dated Sep. 24, 2013 in Int'l Application No. PCT/IL2012/000354.
Office Action dated Feb. 13, 2014 in U.S. Appl. No. 13/884,981, Denenburg.
U.S. Appl. No. 14/345,094, Lev, filed Mar. 14, 2014.
Int'l Search Report and Written Opinion dated Jan. 7, 2014 in Int'l Application No. PCT/IL2012/050721.
English translation of an Office Action dated Jan. 9, 2014 in JP Application No. 2010-526421.
English translation of an Office Action dated Dec. 4, 2013 in CN Application No. 201080051210.3.

(56) References Cited

OTHER PUBLICATIONS

English translation of an Office Action dated Dec. 25, 2013 in CN Application No. 201180006530.1.
Office Action dated Nov. 28, 2013 in IN Application No. 4348/DELNP/2008.
Office Action dated Oct. 8, 2013 in CN Application No. 201080043825.1.
English translation of an Office Action dated Feb. 4, 2014 in JP Application No. 2012-554468.
Office Action dated Jan. 17, 2014 in CN Application No. 201180006534.X.
Int'l Search Report and Written Opinion dated May 8, 2014 in Int'l Application No. PCT/IL2013/050706.
English translation of an Office Action dated Apr. 28, 2014 in JP Application No. 2013-537257.
Int'l Preliminary Report on Patentability dated Jan. 14, 2014 in Int'l Application No. PCT/IL2012/050516.
Office Action dated May 6, 2014 in U.S. Appl. No. 13/505,881, Lev.
U.S. Appl. No. 14/366,306, Lev, filed Jun. 18, 2014.
Office Action dated Apr. 17, 2014 in CN Application No. 201080051201.4.
Int'l Search Report and Written Opinion dated Jul. 16, 2014 in Int'l Application No. PCT/IL2014/050327.
English translation of an Office Action dated Jun. 30, 2014 in CN Application No. 201180052962.6.
Extended European Search Report dated Jun. 3, 2014 in EP Application No. 08781828.2.
Written Opinion dated Jul. 1, 2013 in Int'l Application No. PCT/IL2013/050180.
Int'l Preliminary Report on Patentability dated Apr. 1, 2014 in Int'l Application No. PCT/IL2013/050180.
Written Opinion dated Jul. 31, 2013 in Int'l Application No. PCT/IL2013/050313.
Int'l Preliminary Report on Patentability dated May 12, 2014 in Int'l Application No. PCT/IL2013/050316.
Office Action dated Jul. 31, 2014 in U.S. Appl. No. 29/438,141, Gilboa.
U.S. Appl. No. 14/385,212, Lev, filed Sep. 15, 2014.
U.S. Appl. No. 29/502,037, Lev, filed Sep. 11, 2014.
U.S. Appl. No. 29/502,053, Lev, filed Sep. 11, 2014.
U.S. Appl. No. 14/391,792, Lev, filed Oct. 10, 2014.
U.S. Appl. No. 14/504,979, Lev, filed Oct. 2, 2014.
Int'l Search Report and Written Opinion dated Oct. 17, 2014 in Int'l Application No. PCT/IL2014/050680.
English translation of an Office Action dated Aug. 28, 2014 in JP Application No. 2013-168885.
Written Opinion dated Jun. 5, 2013 in Int'l Application No. PCT/IL2012/050407.
Int'l Preliminary Report on Patentability dated Aug. 20, 2014 in Int'l Application No. PCT/IL2012/050407.
Office Action dated Jan. 2, 2015 in U.S. Appl. No. 29/438,141, Gilboa.
Office Action dated Jan. 5, 2015 in U.S. Appl. No. 29/413,220, Lev.
Office Action dated Jan. 7, 2015 in U.S. Appl. No. 29/438,134, Lev.
U.S. Appl. No. 14/423,595, Lev, filed Feb. 24, 2015.
U.S. Appl. No. 14/423,612, Lev, filed Feb. 24, 2015.
U.S. Appl. No. 14/425,582, Lev, filed Mar. 3, 2015.
Office Action dated Mar. 17, 2015 in U.S. Appl. No. 14/504,979, Lev.
Office Action dated Apr. 9, 2015 in U.S. Appl. No. 13/883,289, Lev.
Office Action dated May 28, 2015 in U.S. Appl. No. 14/391,792, Lev.
Office Action dated Aug. 24, 2015 in U.S. Appl. No. 14/366,306, Lev.
Office Action dated Mar. 10, 2015 in EP Application No. 12 812 395.7.
Office Action dated Aug. 7, 2015 in JP Application No. 2015-529206.
Office Action dated Mar. 1, 2012 in CN Application No. 2008801108283.4.
Office Action dated Mar. 6, 2012 in U.S. Appl. No. 12/678,928.
Int'l Search Report dated Feb. 3, 2011 in Int'l Application No. PCT/IL2010/000777; Written Opinion.
Int'l Search Report dated Mar. 17, 2011 in Intl Application No. PCT/IL2010/000854; Written Opinion.
Int'l Search Report dated Mar. 17, 2011 in Int'l Application No. PCT/IL2010/000915; Written Opinion.
U.S. Appl. No. 13/505,790, Lev, filed May 3, 2012.
U.S. Appl. No. 13/505,881, Lev, filed May 3, 2012.
U.S. Appl. No. 13/522,410, Lev, filed Jul. 16, 2012.
U.S. Appl. No. 13/576,461, Lev, filed Aug. 1, 2012.
Office Action dated Jun. 14, 2012 in U.S. Appl. No. 29/376,980.
Office Action dated Jun. 15, 2012 in U.S. Appl. No. 29/413,170.
Office Action dated Jun. 21, 2012 in U.S. Appl. No. 12/596,167.
Alaris Medical Systems Product Brochure, 4 pages, Issue 1, Oct. 11, 1999.
Smart Site Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with ULTRASITE.RTM. Valve, B. Braun Medical, Inc. website and product description, 3 pages, Feb. 2006.
Int'l Search Report dated Aug. 16, 2012 in Int'l Application No. PCT/IL2012/000164.
U.S. Appl. No. 291438,134, Lev, filed Nov. 27, 2012.
U.S. Appl. No. 291438,141, Gilboa, filed Nov. 27, 2012.
Int'l Search Report dated Jan. 22, 2013 in Int'l Application No. PCT/IL2012/000354.
Int'l Search Report dated Mar. 18, 2013 in Int'l Application No. PCT/IL2012/050516.
Office Action dated Apr. 2, 2013 in U.S. Appl. No. 13/505,790.
Int'l Search Report and Written Opinion dated Mar. 6, 2012 in Int'l Application No. PCT/IL2011/000834.
U.S. Appl. No. 13/883,289, Lev, filed May 3, 2013.
Int'l Search Report & Written Opinion dated Mar. 7, 2012 in Int'l Application No. PCT/IL2011/000829.
U.S. Appl. No. 13/884,981, Denenburg, filed May 13, 2013.
Office Action dated May 31, 2013 in U.S. Appl. No. 13/505,790.
Int'l Search Report dated Jun. 5, 2013 in Int'l Application No. PCT/IL2012/050407.
Int'l Search Report dated Jun. 19, 2013 in Int'l Application No. PCT/IL2013/050167.
Int'l Search Report dated Jul. 1, 2013 in Int'l Application No. PCT/IL2013/050180.
Int'l Search Report dated Jul. 31, 2013 in Int'l Application No. PCT/IL2013/050313.
Int'l Search Report dated Jul. 26, 2013 in Int'l Application No. PCT/IL2013/050316.
English translation of an Office Action dated Jun. 19, 2013 in JP Application No. 2012-531551.
Office Action dated Aug. 20, 2013 in U.S. Appl. No. 13/576,461, Lev.
Int'l Preliminary Report on Patentability dated Aug. 28, 2012 in Int'l Application No. PCT/IL2011/000186.
English translation of an Office Action dated Jul. 26, 2013 in JP Application No. 2012-538464.
International Search Report dated Jan. 23, 2007 in Int'l Application No. PCT/IL/2006/001228.
IV disposables sets catalogue, Cardinal Health, Alaris® products, SmartSite® access devices and accessories product No. 10013365, SmartSite add-on bag access device with spike adapter and needle-free valve bag access port, pp. 1-5, Fall edition (2007).
Drug Administration Systems product information sheets; http://www.westpharma.com/eu/en/products/Pages/Vial2Bag.aspx; pp. 1-3 (admitted prior art).
Office Action dated Jun. 8, 2010 in U.S. Appl. No. 12/112,490, Zinger.
Office Action dated Sep. 28, 2010 in U.S. Appl. No. 12/112,490, Zinger.
Article with picture of West Pharmaceutical Services' Vial2Bag Needleless System, [on-line]; ISIPS Newsletter, Oct. 26, 2007];

(56) References Cited

OTHER PUBLICATIONS retrieved from Internet Feb. 16, 2010]; URL:<http://www.isips.org/reports/ISIPS_Newsletter_October_26_2007. html.> (7 pages. see pp. 5-6).
Office Action dated Jun. 15, 2011 in JP Application No. 2008-538492.
Translation of Office Action dated Jun. 18, 2012 in JP Application No. 2008-538492.
Translation of Office Action dated Apr. 15, 2013 in JP Application No. 2008-538492.
Office Action dated Jul. 13, 2012 in U.S. Appl. No. 12/112,490, Zinger.
Office Action dated Jan. 23, 2013 in U.S. Appl. No. 12/112,490, Zinger.
Int'l Preliminary Report on Patentability dated May 6, 2008 in Int'l Application No. PCT/IL2006/001228.
Written Opinion dated Aug. 16, 2012 in Int'l Application No. PCT/IL2012/000164.
English translation of an Office Action dated Sep. 10, 2013 in JP Application No. 2012-554468.
Written Opinion dated Apr. 10, 2015 in Int'l Application No. PCT/IL2014/050405.
Response to Written Opinion dated Mar. 9, 2015 in Int'l Application No. PCT/IL2014/050405.
U.S. Appl. No. 14/784,300, Lev, filed Oct. 14, 2015.
Office Action dated Oct. 5, 2015 in U.S. Appl. No. 14/385,212, Lev.
Office Action dated Dec. 9, 2015 in U.S. Appl. No. 29/478,723, Lev.
West, Vial2Bag DC system, Oct. 2, 2014, https://web.archive.org/web/20141002065133/http://www.westpharma.com/en/products/Pages/Reconstitutionsystems.aspx.
Youtube.com, Vial2Bag DC, Aug. 21, 2014, https://www.youtube.com/watch?v=FEOkglxNBrs.
Office Action dated Dec. 9, 2015 in U.S. Appl. No. 29/478,726, Lev.
Notice of Allowance dated Jan. 12, 2016 in U.S. Appl. No. 14/385,212, Lev.
Notice of Allowance dated Mar. 17, 2016 in U.S. Appl. No. 29/502,037, Lev.
Office Action dated Mar. 25, 2016 in U.S. Appl. No. 29/478,726, Lev.
Office Action dated Mar. 28, 2016 in JP Application No. 2016-507113.
Int'l Search Report and Written Opinion dated Sep. 14, 2016 in Int'l Application No. PCT/IL2016/050709.
Int'l Search Report and Written Opinion dated Oct. 11, 2016 in Int'l Application No. PCT/IL2016/050782.
Office Action dated Dec. 21, 2016 in IL Application No. 228452.
Extended European Search Report dated Feb. 16, 2017 in EP Application No. 16200458.
Vial-Mate Adapter Device, Baxter, May 2017, downloaded from web page:http://www.baxtermedicationdeliveryproducts.com/drug-delivery/vialmate.html, Download Date: Jul. 28, 2017, original posting date: unknown, 1page.
Office Action dated Aug. 2, 2017 in CN Application No. 201480026311.3.
Int'l Search Report and Written Opinion dated Sep. 2, 2014 in Int'l Application No. PCT/IL2014/050405.
Grifols Vial Adapter Product Literature, 2 pages, Jan. 2002.
Novel Transfer, Mixing and Drug Delivery Systems, MOP Medimop Medical Projects Ltd. Catalog, 4 pages, Rev. 4, 2004.
Office Action dated Oct. 6, 2003 in U.S. Appl. No. 10/062,796.
Office Action dated Feb. 22, 2005 in U.S. Appl. No. 10/062,796.
Office Action dated Oct. 5, 2005 in U.S. Appl. No. 10/062,796.
Office Action dated Feb. 20, 2009 in U.S. Appl. No. 11/694,297.
Int'l Search Report dated Dec. 6, 2006 in Int'l Application No. PCT/IL2006/000912.
Int'l Preliminary Report on Patentability dated Dec. 4, 2007 in Int'l Application No. PCT/IL2006/000912.
http://www.westpharma.com/en/products/Pages/Mixject.aspx (admitted prior art).
http://www.westpharma.com/SiteCollectionDocuments/Recon/mixject%20product%20sheet.pdf; MIXJECT product information sheet pp. 1. (admitted prior art).
Int'l Search Report dated Jul. 27, 2007 in Int'l Application No. PCT/IL2007/000343.
Int'l Preliminary Report on Patentability dated Jun. 19, 2008 in Int'l Application No. PCT/IL2007/000343.
Int'l Search Report dated Mar. 27, 2009 in Int'l Application No. PCT/US2008/070024.
Int'l Search Report dated Oct. 17, 2005 in Int'l Application No. PCT/IL2005/000376.
Int'l Preliminary Report on Patentability dated Jun. 19, 2006 in Int'l Application No. PCT/IL2005/000376.
Written Opinion of ISR dated Jun. 19, 2006 in Int'l Application No. PCT/IL2005/000376.
Int'l Search Report dated Aug. 25, 2008 in Int'l Application No. PCT/IL2008/000517.
Written Opinion of the ISR dated Oct. 17, 2009 in Int'l Application No. PCT/IL08/00517.
Int'l Preliminary Report on Patenability dated Oct. 20, 2009 in Int'l Application No. PCT/IL2008/000517.
Written Opinion of the Int'l Searching Authority dated Oct. 27, 2008 in Int'l Application No. PCT/US2008/070024.
Int'l Search Report dated Mar. 12, 2009 in Int'l Application No. PCT/IL2008/001278.
Office Action dated Jan. 20, 2010 in JP Application No. 2007-510229.
Office Action dated Apr. 20, 2010 in U.S. Appl. No. 11/997,569.
Int'l Search Report dated Nov. 20, 2006 in Int'l Application No. PCT/IL2006/000881.
Office Action dated May 27, 2010 in U.S. Appl. No. 11/559,152.
Decision to Grant mailed Apr. 12, 2010 in EP Application No. 08738307.1.
Office Action dated Jun. 1, 2010 in U.S. Appl. No. 11/568,421.
Office Action dated Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justrice.gov.il/UI/RequestsList.aspx>. (1 page).
Int'l Search Report dated Nov. 25, 2010 in Int'l Application No. PCT/IL2010/000530.
Office Action dated Feb. 7, 2011 in U.S. Appl. No. 12/783,194.
Office Action dated Dec. 20, 2010 in U.S. Appl. No. 12/063,176.
Office Action dated Dec. 13, 2010 in U.S. Appl. No. 12/293,122.
Office Action dated Nov. 29, 2010 in U.S. Appl. No. 11/568,421.
Office Action dated Dec. 23, 2010 in U.S. Appl. No. 29/334,696.
Int'l Search Report dated Mar. 17, 2011 in Int'l Application No. PCT/IL2010/000854.
Overview—Silicone Rubber [retrieved from http://www.knovel.com/web/portal/browse/display?_EXT_KNOVEL_DISPLAY_bookid=1023&VerticalID=0 on Feb. 9, 2011].
Int'l Search Report dated Mar. 17, 2011 in Int'l Application No. PCT/IL2010/00915.
Office Action dated May 12, 2011 in U.S. Appl. No. 12/063,176.
Office Action dated Jul. 11, 2011 in U.S. Appl. No. 12/293,122.
Int'l Search Report dated Jul. 12, 2011 in Int'l Application No. PCT/IL2011/000187.
Int'l Search Report dated Jul. 12, 2011 in Int'l Application No. PCT/IL2011/000186.
Office Action dated Aug. 3, 2011 in JP Application No. 2008-525719.
Int'l Search Report dated Oct. 7, 2011 in Int'l Application No. PCT/IL2011/000511.
Int'l Search Report dated Mar. 6, 2012 in Int'l Application No. PCT/IL2011/000834; Written Opinion.
Office Action dated Mar. 1, 2012 in JP Application No. 2007-510229.

(56) References Cited

OTHER PUBLICATIONS

Int'l Search Report dated Mar. 7, 2012 in Int'l Application No. PCT/IL2011/000829; Written Opinion.
Office Action dated Mar. 13, 2012 in CA Application No. 2,563,643.

* cited by examiner

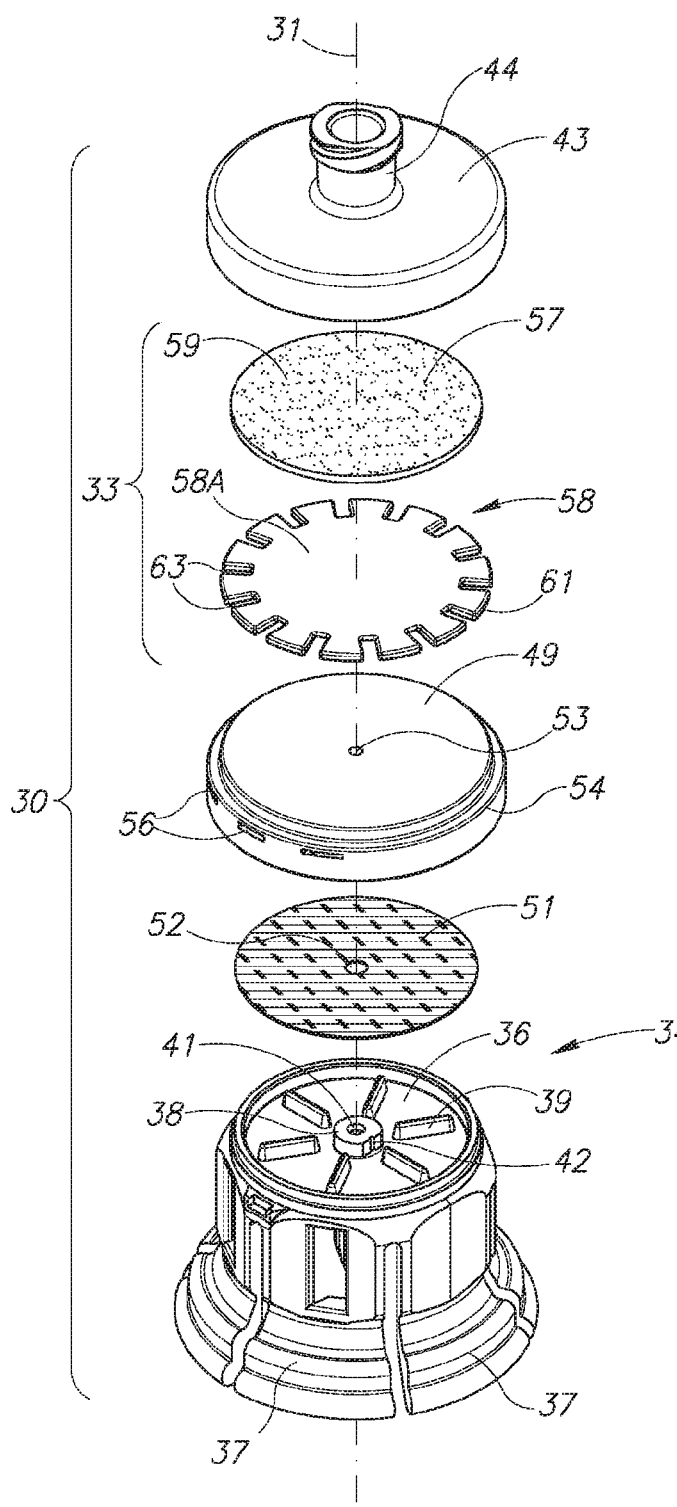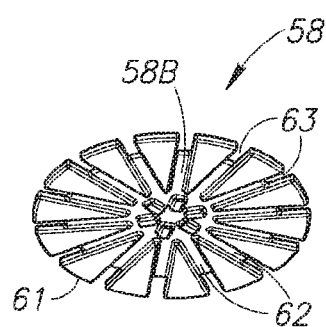
FIG.5
FIG.6

MEDICAL DEVICES INCLUDING VIAL ADAPTER WITH INLINE DRY DRUG MODULE

CROSS-REFERENCE TO RELATED APPLICATIONS

This application is a Section 371 of International Application No. PCT/IL2014/050405, filed May 5, 2014, which was published in the English language on Nov. 13, 2014, under International Publication No. WO 2014/1181328 A1, which claims priority to U.S. Provisional Patent Application No. 61/821,760, filed May 10, 2013, the disclosures of which are incorporated herein by reference.

FIELD OF THE INVENTION

The invention pertains to medical devices with an inline dry drug module including a dry drug dosage for use with a liquid source for parenteral administration to a patient.

BACKGROUND OF THE INVENTION

Medical treatments often involve parenteral administration of liquid drugs to the human body. The liquid drugs can be in the form of solutions, suspensions, and the like. Some drugs reagents have extended shelf-lives in a dry state and only short shelf-lives after reconstitution or rehydration.

U.S. Pat. No. 6,520,932 to Taylor discloses an inline drug delivery pack (35) that connects inline with an intravenous (IV) line and allows for the mixing of diluent with a drug reagent to be delivered to a patient. The drug delivery pack includes a housing (37) with a reagent bed (110) consisting of a fluid soluble material suitable to administration to a patient via dissolution and IV drip. The housing includes inlet radial fins (65) which cooperate with back pressure from an inlet frit (80) to promote a uniform distribution of diluent across the entire cross section of the drug delivery pack. An internal drug bed bypass mechanism is tailored to apportion diluent flow between the bypass and the drug bed to achieve a solution concentration suitable for IV administration as the dried reagent is dissolved.

U.S. Pat. No. 6,951,613 to Reif et al. discloses a genetic vaccination device and a process for forming an injection solution therefor. The device includes a syringe (2) and a cannula (3) coupled to an inline membrane adsorber (5) having genetic material adsorbed thereon. The process includes eluting the genetic material from the membrane adsorber so as to form an injection solution containing the genetic material.

U.S. Patent Application Publication No. US 2008/0294100 to de Costa et al. discloses a pharmaceutical device for the administration of substrates to a patient. The de Costa pharmaceutical device is similar to the aforementioned Reif genetic vaccination device insofar it includes an inline porous membrane supporting a glassy material soluble in water and having biological materials such as vaccines stabilized thereon such that when the biological material requires administration, eluent can be passed across the membrane dissolving the glass and causing the substance to be carried by the liquid into a patient.

The Reif genetic vaccination device and the de Costa pharmaceutical device are relatively heavy and cumbersome to handle during injection of an injection solution to a patient. Furthermore, their device housings containing the dry drug dosage to be injected to a patient necessarily impose injections at larger injection angles to a patient's body than is customary.

There is a need for medical devices with an inline dry drug module for facilitating injecting an injection solution to a patient.

SUMMARY OF THE INVENTION

The present invention is directed toward medical devices including a vial adapter with an inline dry drug module having a dry drug dosage for use with a needleless syringe and a vial for filling the needleless syringe with an injection solution formed from the dry drug dosage for injection to a patient. The medical devices are preferably used with an initially empty needleless syringe and a vial initially filled with a liquid carrier. Alternatively, the medical device can be used with a syringe initially pre-filled with a liquid carrier and an initially empty vial. The liquid carrier can be diluent only or alternatively can include an active component.

The vial adapters have a similar construction as commercially available vented or non-vented vial adapters except for the inline dry drug modules. The inline dry drug modules include a dry drug storage component for storing a dry drug dosage and a uniform carrier liquid distribution component for promoting uniform contact of the dry drug storage component by the carrier liquid to form the injection solution. The dry drug storage component and the uniform carrier liquid distribution component can be two discrete components. Alternatively, the two components can be combined in a single dual purpose component.

The inline dry drug modules can employ any one of several commercially available technologies for enabling long term storage of a dry drug dosage for subsequent forming into an injection solution on contact by a carrier liquid. Suitable commercially available technologies are inter alia discussed in the prior art references acknowledged in the Background of the Invention. The different technologies include inter alia flowing carrier liquid through a porous substrate to dissolve or entrain a dry drug dosage, flowing carrier liquid on a substrate surface to dissolve or entrain a dry drug dosage, and the like.

The use of medical devices of the present invention with an initially empty needleless syringe and an initially filled vial involves a single aspiration. Alternatively, the use of the medical devices of the present invention with an initially filled syringe and an initially empty vial requires an initial injection of a carrier liquid from the syringe to the vial and a subsequent aspiration from the vial to the syringe. The former use takes less time whilst the latter use can afford greater certainty regarding complete usage of a dry drug dosage.

The medical devices of the present invention afford a convenient low cost solution for the preparation of needleless syringes for injection of injection solutions to patients. The medical devices of the present invention are particularly suitable for use with so-called thermo-stable drugs and reagents which have a relatively long shelf-life at ambient temperatures thereby negating the need for refrigeration. Suitable drugs and reagents include inter alia vaccines, and the like.

BRIEF DESCRIPTION OF THE DRAWINGS

In order to understand the invention and to see how it can be carried out in practice, preferred embodiments will now be described, by way of non-limiting examples only, with reference to the accompanying drawings, in which similar parts are likewise numbered, and in which:

FIG. 5 is an exploded view of the FIG. 1 medical device;

FIG. 6 is a bottom perspective view of a uniform carrier liquid distribution component of the FIG. 1 medical device;

DETAILED DESCRIPTION OF THE DRAWINGS

Figure 1:
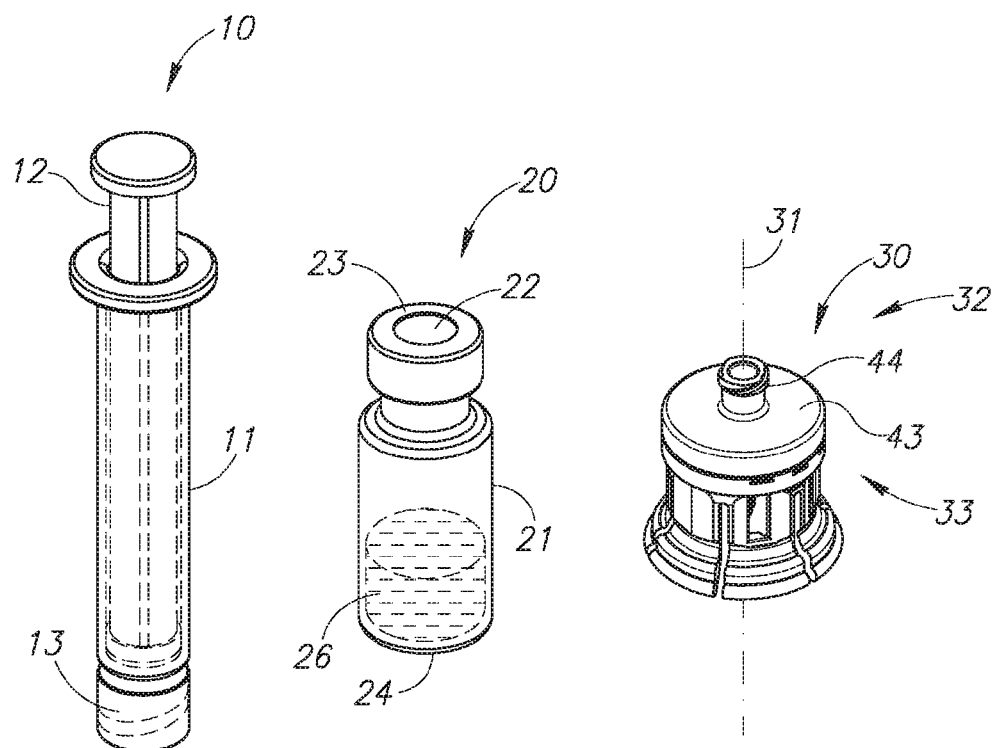
FIG. 1 is a pictorial view of an initially empty needleless syringe, a vial, and a first embodiment of a vented medical device in accordance with the present invention for filling the initially empty needleless syringe with an injection solution.
Figure 2:
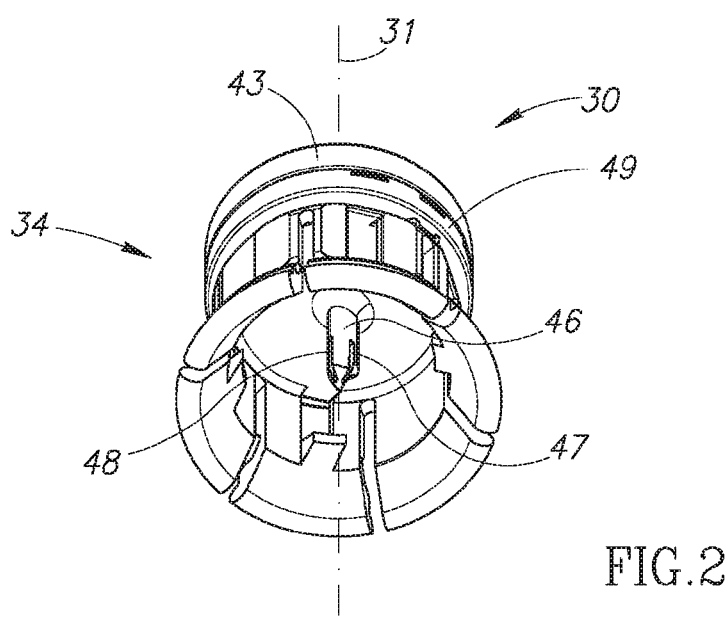
FIG. 2 is a bottom perspective view of the FIG. 1 medical device.
Figure 3:
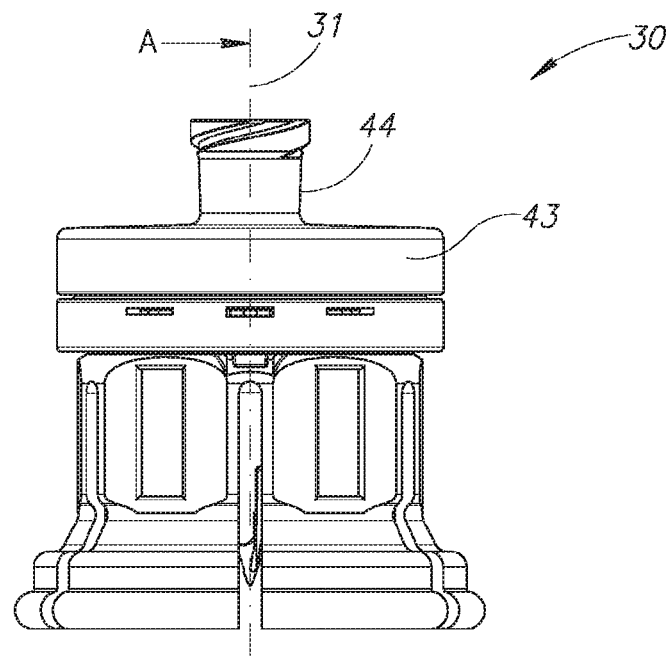
FIG. 3 is a side elevation view of the FIG. 1 medical device.
Figure 4:
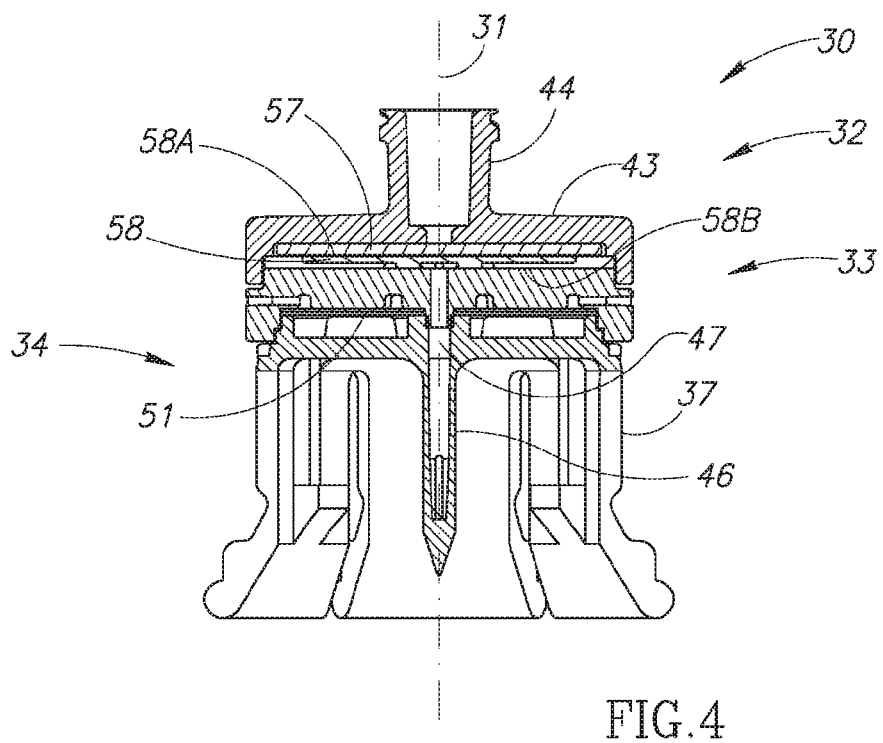
FIG. 4 is a longitudinal cross section of the FIG. 1 medical device along line A-A in FIG. 3.

FIG. 1 shows an empty needleless syringe 10, a vial 20 and a vented medical device 30 for use for filling the needleless syringe 10 with an injection solution for injection to a patient. The syringe 10 includes a barrel 11 with a plunger rod 12 and a syringe tip 13. The vial 20 includes a vial bottle 21 sealed by a vial stopper 22. The vial bottle 21 typically includes an aluminum seal 23 for securing the vial stopper 22 on the vial bottle 21. The vial bottle 21 has a vial interior 24 containing a carrier liquid 26. The carrier liquid 26 can be diluent only. Alternatively, the carrier liquid 26 can include an active component.

FIGS. 1 to 6 show the medical device 30 has a longitudinal device centerline 31 and includes a vial adapter 32 with an inline dry drug module 33. The vial adapter 32 includes a skirt 34 having a transverse top skirt wall 36 and downward depending flex members 37 for telescopic mounting onto the vial 20. The top skirt wall 36 is formed with a central skirt hub 38 co-axial with the longitudinal device axis 31 with six equispaced radial ribs 39 outwardly extending therefrom. The central skirt hub 38 is formed with a liquid transfer port 41 co-axial with the longitudinal device axis 31 and a vent port 42 offset with respect to the longitudinal device axis 31.

The vial adapter 32 includes a top cover 43 having a central upright female connector 44 co-axial with the longitudinal device centerline 31 for sealing connection with the syringe tip 13. The syringe tip 13 is preferably a male Luer lock connector and the central upright female connector 44 is a female Luer connector for screw thread mounting of the needleless syringe 10 on the medical device 30. Alternatively, the syringe tip 13 and the female connector 44 can be formed with other connectors.

The vial adapter 32 includes a downward depending puncturing cannula 46 co-axial with the longitudinal device 31 for puncturing the vial stopper 22 for flow communication with the vial interior 24 on telescopic mounting the medical device 30 on the vial 20. The cannula 46 includes a liquid transfer lumen 47 in flow communication with the liquid transfer port 41 and a vent lumen 48 in flow communication with the vent port 42.

The vial adapter 32 includes a filter cover 49 for deployment between the top cover 43 and the top skirt wall 36. The filter cover 49 encloses an air filter 51 placed on the radial ribs 39. The air filter 51 has a central air filter aperture 52 co-axial with the longitudinal device axis 31. The filter cover 49 includes a central filter cover aperture 53 co-axial with the longitudinal device axis 31 and a peripheral filter cover edge 54 formed with a multitude of vent apertures 56.

The inline dry drug module 33 is disposed inline between the central upright female connector 44 and the puncturing cannula 46 and in particular the liquid transfer port 41. The inline dry drug module 33 includes a dry drug storage component 57 proximate the upright female connector 44 and distal from the puncturing cannula 46. The inline dry drug module 33 further includes a uniform carrier liquid distribution component 58 proximate the puncturing cannula 46 and distal from the upright female connector 44.

The dry drug storage component 57 is preferably formed as a disc-like substrate formed from a wide range of suitable bio-compatible inert porous materials enabling carrier liquid 26 to flow therethrough. Suitable materials include inter alta glass fiber, plastic fiber, and the like. The dry drug storage component 57 is provisioned with a dry drug dosage 59 for administration to a patient. The dry drug dosage 59 can be in the form of very fine particles, and the like, for enabling reconstitution of an injection solution on entraining carrier liquid 26 through the dry drug storage component 57.

The uniform carrier liquid distribution component 58 is preferably formed as a disc-like member having a uniform carrier liquid distribution component topside 58A facing the upright female connector 44, a uniform carrier liquid distribution component underside 58B facing the puncturing cannula 46, and a uniform carrier liquid distribution component peripheral edge 61. The uniform carrier distribution component underside 58B is formed with a series of radial grooves 62 each terminating at a cutout 63 in the uniform carrier liquid distribution component peripheral edge 61 for enabling flow communication from the uniform carrier liquid distribution component underside 58B to the uniform carrier liquid distribution component topside 58A.

Figures 7A, 7B, 7C:
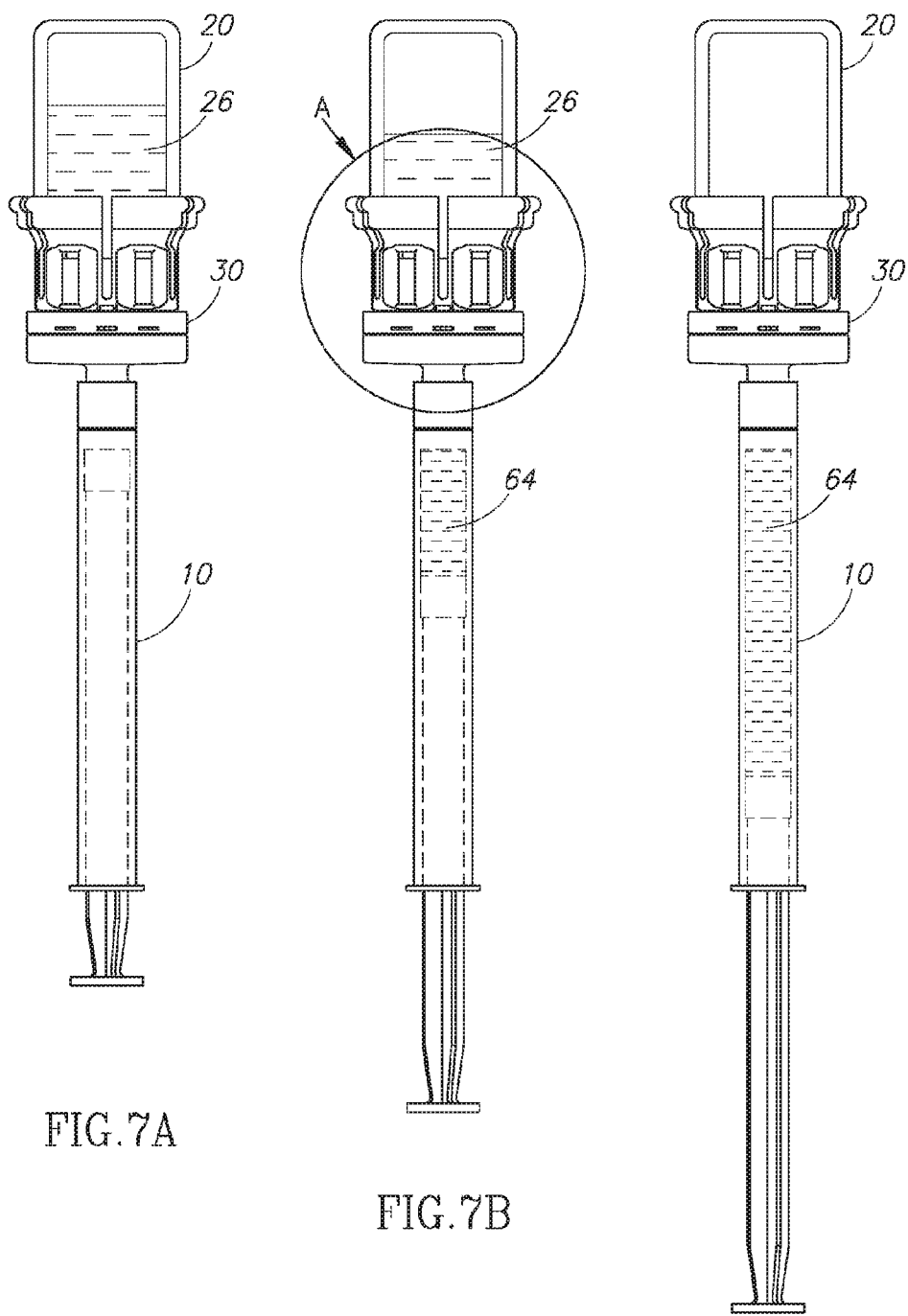
FIG. 7A shows an inverted assemblage of the initially empty needleless syringe, the FIG. 1 medical device and the vial prior to aspiration of carrier liquid from the vial to the needleless syringe.
FIG. 7B shows the inverted assemblage subsequent to partial aspiration of carrier liquid from the vial to the needleless syringe.
FIG. 7C shows the inverted assemblage with the needleless syringe filled with injection solution for administration to a patient.

The use of the medical device 30 for use in the preparation of the needleless syringe 10 with an injection solution for injection to a subject is now described with reference to FIGS. 7A to 7C and FIG. 8 which is an enlargement of the encircled area denoted A in FIG. 7B:

FIG. 7A shows a user telescopically mounts the medical device 30 onto the vial 20 to puncture the vial stopper 22. The user connects the needleless syringe 10 to the female connector 44. The user inverts the assemblage such that the vial 20 is above the needleless syringe 10 and begins to aspirate the carrier liquid 26 from the vial 20 into the needleless syringe 10.

Figure 8:
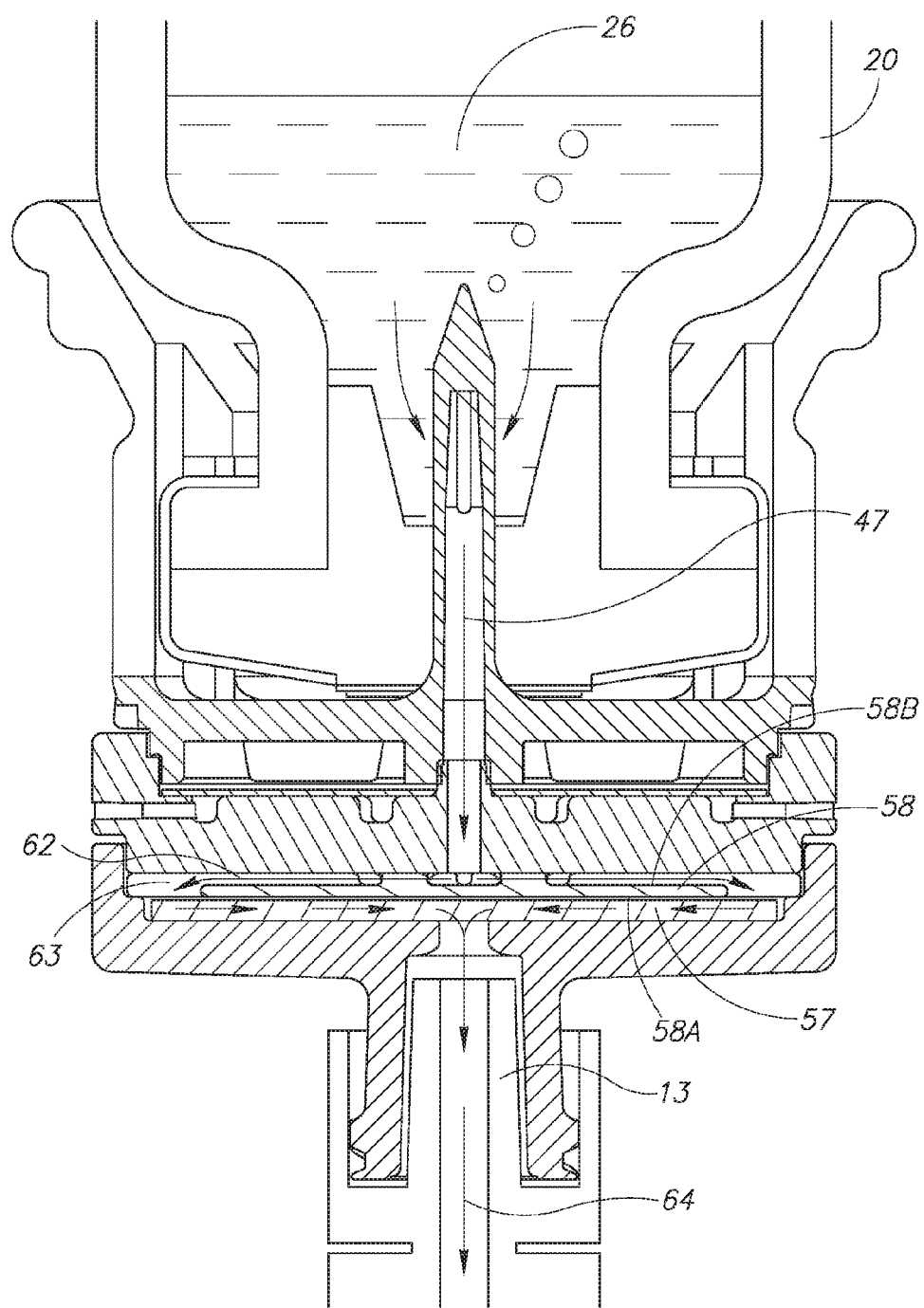
FIG. 8 is a close up longitudinal cross section of the encircled section of FIG. 7B's assemblage showing the flow of carrier liquid from the vial to the syringe during aspiration.

FIG. 7B and FIG. 8 show the flow of carrier liquid 26 from the vial 20 to the initially empty needleless syringe 10 as follows: The carrier liquid 26 flows downward along the liquid transfer lumen 47 to the uniform carrier liquid distribution component underside 58B. The carrier liquid 26 flows radial outward from the center of the uniform carrier liquid distribution component underside 58B along the radial grooves 62 to the uniform carrier liquid distribution component peripheral edge 61.

The carrier liquid 26 flows downward through the cutouts 63 and then radial inwards through the porous dry drug storage component 57 to entrain the dry drug dosage 59 therewith to form an injection solution 64. During aspiration of the carrier liquid 26 from the vial 20 to the syringe 10, air is drawn through the vent apertures 56, the air filter 51 and the vent lumen 48 into the vial 20 as indicated by air bubbles in the carrier liquid 26.

FIG. 7C shows the syringe 10 filled with an injection solution 64 ready for injection to a subject after disconnection from the female connector 44 and attachment of a needle.

Figures 9, 10:
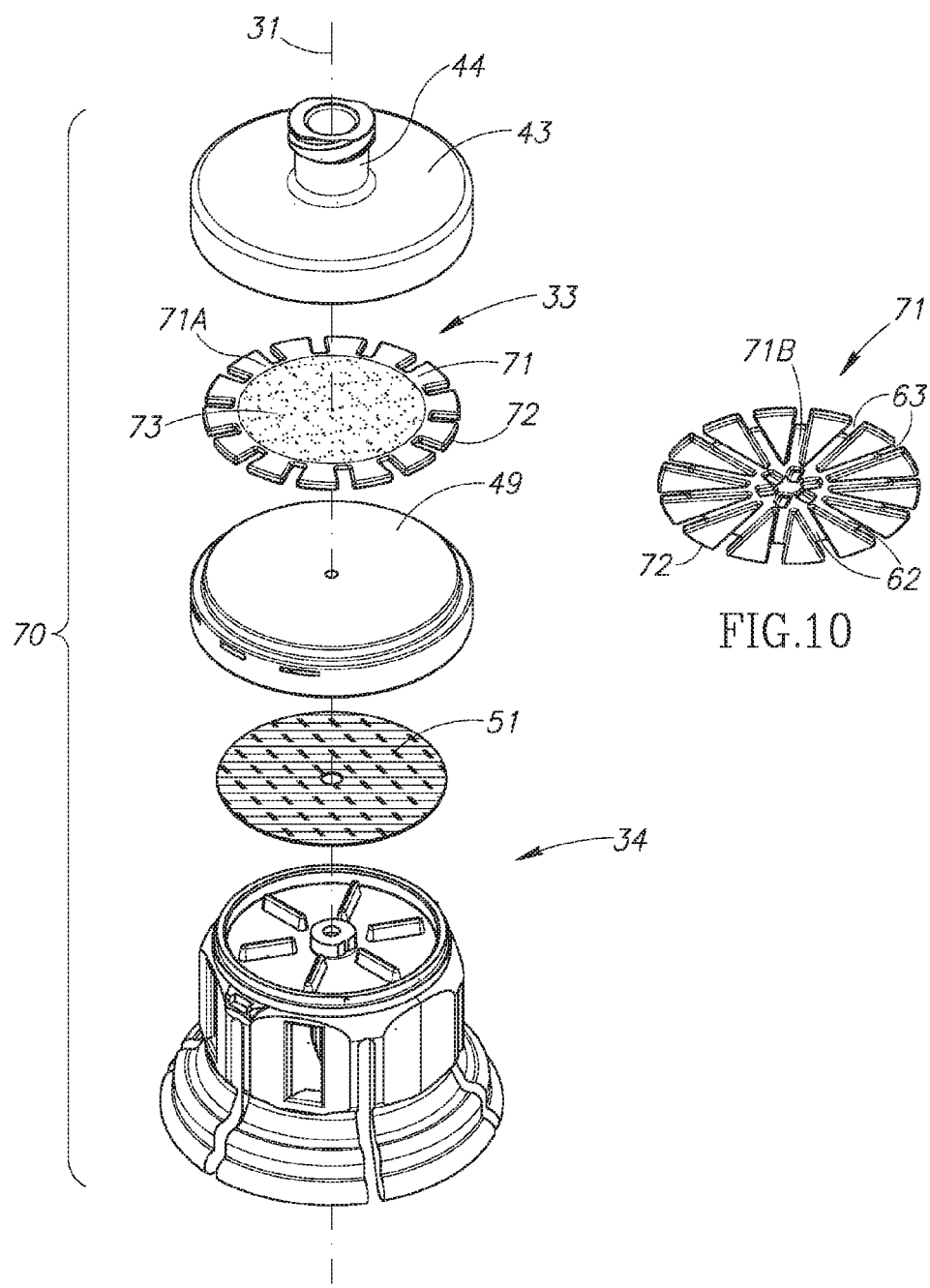
FIG. 9 is an exploded view of a second embodiment of a vented medical device in accordance with the present invention.
FIG. 10 is a bottom perspective view of a uniform carrier liquid distribution component of the FIG. 9 medical device.

FIG. 9 shows a vented medical device 70 similar in construction and operation as the vented medical device 30 and therefore similar parts are likewise numbered. The latter 70 differs from the former 30 insofar its inline dry drug module 33 includes a single dual purpose component 71 acting as both a dry drug dosage storage component and a uniform carrier liquid distribution component. The dual purpose component 71 has a similar construction as the uniform carrier liquid distribution component 58 insofar as it includes a uniform carrier liquid distribution component topside 71A facing the female connector 44, a uniform carrier liquid distribution component underside 71B facing the puncturing cannula 46 and a uniform carrier liquid distribution component peripheral edge 72. The uniform carrier liquid distribution component topside 71A has a dry drug dosage coating 73 constituting a dry drug dosage storage component. The uniform carrier distribution component underside 71B is formed with a series of radial grooves 62 each terminating at a cutout 63 in the uniform carrier liquid distribution component peripheral edge 72 for enabling flow communication from the uniform carrier liquid distribution component underside 71B to the uniform carrier liquid distribution component topside 71A.

While the invention has been described with respect to a limited number of embodiments, it will be appreciated that many variations, modifications, and other applications of the invention can be made within the scope of the appended claims.

The invention claimed is:
1. A medical device for use with a needleless syringe, a vial and a carrier liquid for filling the needleless syringe with an injection solution for injection to a patient, the needleless syringe having a male connector, the vial having a vial stopper and a vial interior, the medical device having a longitudinal device axis and comprising:
 (a) a vial adapter having a skirt with downward depending flex members for telescopic mounting on the vial, a puncturing cannula for puncturing the vial stopper on said telescopic mounting for flow communication with the vial interior and a central upright female connector in flow communication with said puncturing cannula and intended for connection to the male connector; characterized by
 (b) an inline dry drug module disposed inline between said female connector and said puncturing cannula, said inline dry drug module including a dry drug storage component storing a dry drug dosage and a uniform carrier liquid distribution component for promoting uniform contact of said dry drug storage component by said carrier liquid on aspiration of carrier liquid from the vial through the inline dry drug module directly to the needleless syringe to form the injection solution.

2. The device according to claim 1, wherein said inline dry drug module includes a discrete dry drug storage component for storing said dry drug dosage and a discrete uniform carrier liquid distribution component for promoting said uniform contact.

3. The device according to claim 1, wherein said inline dry drug module includes a dual purpose component for both storing said dry drug dosage and promoting said uniform contact.

4. The device according to claim 3, wherein the uniform carrier liquid component includes a uniform carrier liquid component topside facing said female connector, a uniform carrier liquid distribution component underside facing said puncturing cannula and a uniform carrier liquid distribution component peripheral edge,
 wherein said uniform carrier liquid distribution component topside has a dry drug dosage coating constituting the dry drug storage component.

5. The device according to claim 4, wherein the uniform carrier liquid distribution component underside is formed with a series of radial grooves each terminating at the cutout in the uniform carrier liquid distribution component peripheral edge for enabling flow communication from the uniform carrier liquid distribution component underside to the uniform carrier liquid distribution component topside on aspiration of the needleless syringe to draw liquid contents from the vial through the inline dry drug module directly to the needleless syringe.

6. The device according to claim 1, wherein said, uniform carrier liquid component includes a uniform carrier liquid component topside facing said female connector, a uniform carrier liquid distribution component underside facing said puncturing cannula and a uniform carrier liquid distribution component peripheral edge,
 said uniform carrier liquid distribution component underside having a multitude of radial grooves each terminating in a cutout in said uniform carrier liquid distribution component peripheral edge thereby enabling carrier liquid to flow from said uniform carrier liquid distribution component underside to said uniform carrier liquid distribution component topside on aspiration of the needleless syringe to draw liquid contents from the vial through the inline dry drug module directly to the needleless syringe.

\* \* \* \* \*

UNITED STATES PATENT AND TRADEMARK OFFICE
CERTIFICATE OF CORRECTION

PATENT NO. : 9,943,463 B2
APPLICATION NO. : 14/888590
DATED : April 17, 2018
INVENTOR(S) : Hugh Zachary Marks et al.

Page 1 of 1

It is certified that error appears in the above-identified patent and that said Letters Patent is hereby corrected as shown below:

In the Claims

In Claim 6, delete the phrase "wherein said, uniform" at Column 6, Line 42, and insert the phrase "wherein said uniform".

Signed and Sealed this
Nineteenth Day of June, 2018

Andrei Iancu
*Director of the United States Patent and Trademark Office*